US007087249B2

(12) United States Patent
Burrell et al.

(10) Patent No.: US 7,087,249 B2
(45) Date of Patent: Aug. 8, 2006

(54) TREATMENT OF MUCOSAL MEMBRANES

(75) Inventors: Robert Edward Burrell, Sherwood Park (CA); Antony George Naylor, Sherwood Park (CA); Peter Howard Moxham, Sherwood Park (CA)

(73) Assignee: Nucryst Pharmaceuticals Corp., Alberta (CA)

(*) Notice: Subject to any disclaimer, the term of this patent is extended or adjusted under 35 U.S.C. 154(b) by 0 days.

(21) Appl. No.: 10/131,509

(22) Filed: Apr. 23, 2002

(65) Prior Publication Data

US 2003/0099718 A1 May 29, 2003

Related U.S. Application Data

(63) Continuation-in-part of application No. 09/840,637, filed on Apr. 23, 2001.

(60) Provisional application No. 60/285,884, filed on Apr. 23, 2001.

(51) Int. Cl.

| | |
|---|---|
| *A61K 9/00* | (2006.01) |
| *A61K 9/02* | (2006.01) |
| *A61K 9/14* | (2006.01) |
| *A61K 9/70* | (2006.01) |
| *A61K 9/72* | (2006.01) |
| *A61K 31/28* | (2006.01) |
| *A61K 31/282* | (2006.01) |
| *A61K 33/24* | (2006.01) |
| *A61K 33/38* | (2006.01) |
| *A61P 11/00* | (2006.01) |

(52) U.S. Cl. ....................... 424/618; 424/433; 424/434; 424/435; 424/436; 424/443; 424/457; 424/458; 424/468; 424/469; 424/489; 424/490; 424/617; 424/619; 424/646; 424/649; 424/DIG. 15; 424/400; 424/402; 424/404; 424/405; 514/184; 514/492; 514/495; 514/826; 514/849; 514/851; 514/853; 514/882; 514/886; 514/887; 514/900; 514/901; 514/902; 514/912; 514/914; 514/925; 514/931; 514/932; 514/933; 514/934; 514/951; 514/953; 514/954; 514/956; 514/958; 514/964; 514/965; 514/966; 514/967; 514/968; 514/969

(58) Field of Classification Search ................. 424/400, 424/402, 404, 405, 433–436, 443, 457, 458, 424/468, 469, 489, 490, 617–619, 646, 649, 424/DIG. 15; 514/184, 492, 495, 826, 849, 514/851, 853, 882, 886, 887, 900–902, 912, 514/914, 925, 931–934, 951, 953, 954, 956, 514/958, 964, 965–969, 825

See application file for complete search history.

(56) References Cited

U.S. PATENT DOCUMENTS

| | | | | |
|---|---|---|---|---|
| 3,757,786 | A | 9/1973 | Smith | |
| 3,800,792 | A | 4/1974 | McKnight et al. | 128/156 |
| 3,918,446 | A | 11/1975 | Buttaravoli | |
| 3,988,434 | A | 10/1976 | Schole et al. | 424/54 |
| 4,059,105 | A | 11/1977 | Citruzzula et al. | |
| 4,324,237 | A | 4/1982 | Buttaravoli | |

(Continued)

FOREIGN PATENT DOCUMENTS

| | | |
|---|---|---|
| CA | 2242033 | 1/1999 |
| CN | 1082645 | 2/1994 |
| CN | 1241662 | 1/2000 |
| CN | 1262093 | 8/2000 |
| CN | 1279222 | 1/2001 |

(Continued)

OTHER PUBLICATIONS

Chemical Abstracts 25:2814a (1931).*

Derwent Abstract, accession No. 2000-161633, abstracting: CN 1236620 (Dec. 1999).*

Chemical Abstracts 111:127022 (1989).*

Derwent Abstract, accession No. 1996-186468, abstracting: RU 2042352 (Aug. 1995).*

WPIDS abstract 1966-11488F (1966).*

WPIDS abstract 1989-312257 (1989).*

Medline abstract, accession No. 96064219 (1996).*

Shigemasa et al., "Applications of Chitin and Chitosan for Biomaterials" *Biotechnology & Genetic Engineering Reviews* vol. 13 (14) pp. 383–420.

Thornton, "Deposition Technologies for Films and Coatings: Coating Deposition by Sputtering" *Materials Science Series* 5 pp. 170–243 1982.

Burrell, et al. "Efficacy of Silver-Coated Dressings as Bacterial Barriers in a Rodent Burn Sepsis Model" *Wounds* 1999; 11(4): 64–71.

Demling, et al., "The Role of Silver in Wound Healing: Effects of Silver on Wound Management," *Wounds*, vol. 13, No. 1, Jan./Feb. 2001 Supplement A; pp. 5–14.

Djokic et al., "An Electrochemical Analysis of Thin Silver Films Produced by Reactive Sputtering", *Journal of The Electrochemical Society*, 148 (3) C191–C196 (2001).

Kirsner, et al., "The Role of Silver in Wound Healing: Matrix Metalloproteinases in Normal and Impaired Wound Healing: A Potential Role of Nanocrystalline Silver," *Wounds*, vol. 13, No. 3, May/Jun. 2001, Supplement C pp. 5–12.

(Continued)

*Primary Examiner*—John Pak
(74) *Attorney, Agent, or Firm*—Fish & Richardson P.C.

(57) ABSTRACT

The invention relates to the use of one or more antimicrobial metals preferably selected from silver, gold, platinum, and palladium but most preferably silver, formed with atomic disorder, and preferably in a nanocrystalline form, for reducing inflammation or infection of the mucosal membrane. The antimicrobial metal may be formulated as, or used in the form of, a nanocrystalline coating of one or more antimicrobial or noble metals, a nanocrystalline powder of one or more antimicrobial or noble metals, or a liquid or solution containing dissolved species from a nanocrystalline powder or coating of one or more antimicrobial or noble metals.

28 Claims, No Drawings

U.S. PATENT DOCUMENTS

| | | | | |
|---|---|---|---|---|
| 4,355,636 | A | 10/1982 | Oetjen et al. | 128/204.13 |
| 4,476,590 | A | 10/1984 | Scales et al. | |
| 4,581,028 | A | 4/1986 | Fox, Jr. et al. | |
| 4,596,556 | A | 6/1986 | Morrow et al. | |
| 4,633,863 | A | 1/1987 | Filips et al. | |
| 4,749,572 | A | 6/1988 | Ahari | 424/132 |
| 4,790,824 | A | 12/1988 | Morrow et al. | |
| 4,803,066 | A | 2/1989 | Edwards | 424/132 |
| 4,828,832 | A | 5/1989 | De Cuellar et al. | |
| 4,847,049 | A | 7/1989 | Yamamoto | |
| 4,952,411 | A | 8/1990 | Fox, Jr. et al. | 424/618 |
| 4,960,413 | A | 10/1990 | Sagar et al. | |
| 5,019,096 | A | 5/1991 | Fox, Jr. et al. | |
| 5,064,413 | A | 11/1991 | McKinnon et al. | |
| 5,122,418 | A | 6/1992 | Nakane et al. | |
| 5,143,717 | A | 9/1992 | Davis | 424/45 |
| 5,236,421 | A | 8/1993 | Becher | |
| 5,270,358 | A | 12/1993 | Asmus | |
| 5,312,335 | A | 5/1994 | McKinnon et al. | |
| D349,958 | S | 8/1994 | Hollis et al. | |
| 5,369,155 | A | 11/1994 | Asmus | |
| 5,372,589 | A | 12/1994 | Davis | |
| 5,383,851 | A | 1/1995 | McKinnon, Jr. et al. | |
| 5,399,163 | A | 3/1995 | Peterson et al. | |
| 5,454,886 | A | 10/1995 | Burrell et al. | |
| 5,454,889 | A | 10/1995 | McNicol et al. | |
| 5,457,015 | A | 10/1995 | Boston | |
| 5,520,639 | A | 5/1996 | Peterson et al. | |
| 5,534,288 | A | 7/1996 | Gruskin et al. | |
| 5,563,132 | A | 10/1996 | Bodaness | |
| 5,569,207 | A | 10/1996 | Gisselberg et al. | |
| 5,578,073 | A | 11/1996 | Haimovich et al. | |
| 5,631,066 | A | 5/1997 | O'Brien | |
| 5,681,575 | A | 10/1997 | Burrell et al. | |
| 5,744,151 | A | 4/1998 | Capelli | 424/405 |
| 5,753,251 | A | 5/1998 | Burrell et al. | |
| 5,770,255 | A | 6/1998 | Burrell et al. | 427/2.1 |
| 5,770,258 | A | 6/1998 | Takizawa | |
| 5,792,793 | A | 8/1998 | Oda et al. | 514/495 |
| 5,837,275 | A | 11/1998 | Burrell et al. | |
| 5,848,995 | A | 12/1998 | Walder | |
| 5,895,419 | A | 4/1999 | Tweden et al. | |
| 5,899,880 | A | 5/1999 | Bellhouse et al. | |
| 5,945,032 | A | 8/1999 | Breitenbach et al. | 252/186.29 |
| 5,958,440 | A | 9/1999 | Burrell et al. | |
| 5,965,610 | A | 10/1999 | Corbin et al. | |
| 5,981,822 | A | 11/1999 | Addison | |
| 5,985,308 | A | 11/1999 | Burrell et al. | |
| 6,010,478 | A | 1/2000 | Bellhouse et al. | |
| 6,013,050 | A | 1/2000 | Bellhouse et al. | |
| 6,017,553 | A | 1/2000 | Burrell et al. | |
| 6,022,547 | A | 2/2000 | Herb et al. | 424/401 |
| 6,071,541 | A | 6/2000 | Murad | 424/616 |
| 6,071,543 | A | 6/2000 | Thornfeldt | 424/642 |
| 6,096,002 | A | 8/2000 | Landau | |
| 6,123,925 | A | 9/2000 | Barry et al. | |
| 6,126,931 | A | 10/2000 | Sawan et al. | 424/78.09 |
| 6,165,440 | A | 12/2000 | Esenaliev | |
| 6,187,290 | B1 | 2/2001 | Gilchrist et al. | 424/45 |
| 6,197,351 | B1 | 3/2001 | Neuwirth | 424/618 |
| 6,201,164 | B1 | 3/2001 | Wulff et al. | |
| 6,224,898 | B1 | 5/2001 | Balogh et al. | 424/445 |
| 6,238,686 | B1 | 5/2001 | Burrell et al. | |
| 6,258,385 | B1 | 7/2001 | Antelman | 424/618 |
| 6,277,169 | B1 | 8/2001 | Hampden-Smith et al. | 75/336 |
| 6,294,186 | B1 | 9/2001 | Beerse et al. | |
| 6,333,093 | B1 | 12/2001 | Burrell et al. | |
| 6,365,130 | B1 | 4/2002 | Barry et al. | 424/48 |
| 6,720,006 | B1 * | 4/2004 | Hanke et al. | 424/484 |
| 2001/0010016 | A1 | 7/2001 | Modak et al. | |
| 2002/0001628 | A1 | 1/2002 | Ito | 424/618 |
| 2002/0016585 | A1 | 2/2002 | Sachse | |
| 2002/0025344 | A1 | 2/2002 | Newman et al. | 424/618 |
| 2002/0045049 | A1 | 4/2002 | Madsen | |
| 2002/0051824 | A1 | 5/2002 | Burrell et al. | |
| 2002/0192298 | A1 | 12/2002 | Burrell et al. | |

FOREIGN PATENT DOCUMENTS

| | | | |
|---|---|---|---|
| CN | 1291666 | | 4/2001 |
| CN | 1291667 | | 4/2001 |
| CN | 1306117 | | 8/2001 |
| CN | 1322474 | | 11/2001 |
| CN | 1322874 | | 11/2001 |
| CN | 1328819 | | 1/2002 |
| CN | 1328827 | | 1/2002 |
| DE | 2748882 | | 5/1979 |
| DE | 3807944 | | 9/1989 |
| DE | 195 41 735 | A1 | 5/1997 |
| EP | 136 768 | | 4/1985 |
| EP | 254 413 | | 1/1988 |
| EP | 0 254 413 | A2 | 1/1988 |
| EP | 0 356 060 | | 8/1989 |
| EP | 355 009 | | 2/1990 |
| EP | 378 147 | | 7/1990 |
| EP | 599 188 | | 6/1994 |
| EP | 0681841 | | 11/1995 |
| EP | 0 681 841 | A1 | 11/1995 |
| EP | 0 439 513 | B1 | 3/1996 |
| EP | 0780138 | | 6/1997 |
| EP | 0 328 421 | A2 | 8/1999 |
| EP | 1 159 972 | | 12/2001 |
| GB | 420052 | | 11/1934 |
| GB | 427106 | | 4/1935 |
| GB | 965010 | | 7/1964 |
| GB | 1270410 | | 4/1972 |
| GB | 2 073 024 | | 10/1981 |
| GB | 2 140 684 | | 12/1984 |
| HU | 980078 | A | 9/1999 |
| IT | 22309A/90 | | 12/1990 |
| JP | 60-21912 | | 2/1985 |
| JP | SHO 58-126910 | | 2/1985 |
| JP | 04244029 | A | 9/1992 |
| JP | 11060493 | | 3/1999 |
| JP | 11 060493 | A | 3/1999 |
| JP | 11116488 | | 4/1999 |
| JP | 11 116488 | | 4/1999 |
| JP | 11 124335 | | 5/1999 |
| JP | 11124335 | | 5/1999 |
| JP | 2000-327578 | | 11/2000 |
| JP | 2000 327578 | | 11/2000 |
| JP | 2000327578 | | 11/2000 |
| WO | WO 87/07251 | | 12/1987 |
| WO | WO 89/09054 | | 10/1989 |
| WO | 92/13491 | | 8/1992 |
| WO | WO 93/23092 | | 11/1993 |
| WO | 93/23092 | | 11/1993 |
| WO | WO 95/13704 | | 5/1995 |
| WO | 95/13704 | | 5/1995 |
| WO | WO 96/17595 | | 6/1996 |
| WO | WO 95/13704 | | 5/1998 |
| WO | WO 98/22116 | | 5/1998 |
| WO | WO 98/41095 | | 9/1998 |
| WO | 98/41095 | | 9/1998 |
| WO | WO 98/51273 | | 11/1998 |
| WO | WO 99/08691 | | 2/1999 |
| WO | WO 00/27390 | | 5/2000 |
| WO | 00/27390 | | 5/2000 |
| WO | 00/30697 | | 6/2000 |
| WO | WO 00/44414 | | 8/2000 |
| WO | 00/64505 | | 11/2000 |
| WO | 00/64506 | | 11/2000 |

| | | | |
|---|---|---|---|
| WO | WO 00/78281 | | 12/2000 |
| WO | WO 00/78282 | | 12/2000 |
| WO | WO 01/15710 | | 3/2001 |
| WO | 01/24839 | | 4/2001 |
| WO | WO 01/26627 | | 4/2001 |
| WO | 01/27365 | | 4/2001 |
| WO | 01/34686 | | 5/2001 |
| WO | 01/41774 | | 6/2001 |
| WO | 01/41819 | | 6/2001 |
| WO | WO 01/43788 | | 6/2001 |
| WO | WO 01/49115 | | 7/2001 |
| WO | 01/49301 | | 7/2001 |
| WO | WO 01/49301 | | 7/2001 |
| WO | WO 01/49302 | | 7/2001 |
| WO | WO 01 49303 | A | 7/2001 |
| WO | WO 01/49303 | | 7/2001 |
| WO | 01/68179 | A1 | 9/2001 |
| WO | WO 01/70052 | | 9/2001 |
| WO | WO 01/74300 | | 10/2001 |
| WO | 01/80920 | | 11/2001 |
| WO | WO 01/93878 | | 12/2001 |
| WO | WO 01/93878 | A2 | 12/2001 |
| WO | 02/09729 | | 2/2002 |
| WO | WO 02/09729 | A2 | 2/2002 |
| WO | 02/15698 | | 2/2002 |
| WO | 02/18003 | | 3/2002 |
| WO | WO 02/18699 | | 3/2002 |
| WO | WO 02/44625 | | 6/2002 |

OTHER PUBLICATIONS

Olson et al., "Healing of Porcine Donor sites Covered with Silver–coated Dressings"* *Eur J Surg* 2000; 166: 486–489.

Ovington, "The Role of Silver in Wound Healing: Why is Nanocrystalline Silver Superior? Nanocrystalline Silver: Where the Old and Familiar Meets a New Frontier," *Wounds*, vol. 13, No. 2, Mar./Apr. 2001, Supplement B; pp. 5–10.

Sant et al., "Novel duplex antimicrobial silver films deposited by magnetron sputtering", *Philosophical Magazine Letters*, 2000, vol. 80, No. 4, 249–256.

Tredget, "Evaluation of Wound Healing using Silver Dressing", Feb. 26, 1996.

Tredget et al., "A Matched–Pair, Randomized Study Evaluating the Efficacy and Safety of Acticoat* Silver–Coated Dressing for the Treatment of Burn Wounds," *Journal of Burn Care & Rehabilitation* Nov./Dec. 1998; 19:531–7.

Voigt, et al., "The Use of Acticoat as Silver Impregnated Telfa Dressings in a Regional Burn and Wound Care Center: The Clinicians View," *Wounds*, vol. 13, No. 2, Mar./Apr. 2001, Supplement B; pp. 11–20.

Wright et al., "Early healing events in a procine model of contaminated wounds: effects of nanocrystalline silver on matrix metalloproteinases, cell apoptosis, and healing" *Wound Repair and Regeneration* 2002; 10:141–151.

Wright, et al., "The Comparative Efficacy of Two Antimicrobial Barrier Dressings: In–vitro Examination of Two Controlled Release of Silver Dressings" *Wounds* vol. 10, No. 6 Nov./Dec. 1998, pp. 179–188.

Wright, et al., "Efficacy of topical silver against fungal burn wound pathogens", *AJIC* vol. 27, No. 4, Aug. 1999.

Wright, et al., "Wound Management in an era of increasing bacterial antibiotic resistance: a role for topical silver treatment," *AJIC* vol. 26, No. 6; pp. 572–577 Dec. 1998.

Yin et al., "Comparative Evaluation of the Antimicrobial Activity of ACTICOAT* Antimicrobial Barrier Dressing" *Journal of Burn Care & Rehabilitation*, vol. 20, No. 3 May/Jun. 1999.

Yin, et al., "Effect of Acticoat Antimicrobial Barrier Dressing on Wound Healing and Graft Take", *Burn Care & Rehabilitation*, part 2 Jan./Feb. 1999.

Rodrigues et al., "Role of lysosomes on human ulcerogenic gastropathies. Effect of zinc ion on the lysosomal stability" *Arquivos de Gastroenterologia 35:4: pp. 247–251* (1998) Abstract only.

Merle E. Olson et al; "Healing of Porcine Donor Sites Covered with Silver–Coated Dressings", Eur J Surg 2000; 166: 486–489.

John A. Thornton; "Influence of Apparatus Geometry and Deposition Conditions on the Structure and Topography of Thick Sputtered Coatings", J. Vac. Sci. Technol. vol. 11, No. 4 Jul./Aug. 1974 p. 666–670.

Database Biosis, Online! Biosciences Information Service, Philadelphia PA, US, Oct. 1998 (1998–1). XP–002214209. Rodrigues, Luiz Erlon A et al; "Role of lysosomes on human ulcerogenic gastropathies. Effect of zinc ion on the lysosomal stability." *Arquivos de Gastroenterologi*, 35:4: 247–251 (1998) (abstract only).

Database WPI, Section Ch. Week 199919, Dewent Publication Ltd., London, GB, AN 1999–226104. XP00224210 and JP 11 060493. Tskiji, E; Mar. 2, 1999 (abstract only).

Sant et al., "Morphology of Novel Antimicrobial Silver Films Deposited By Magnetron Sputtering" *Scripta Materiala*, vol. 41, No. 12, pp. 1333–1339, Nov. 19, 1999.

Derwent Abstract 1994–192726, 1994.

Medline abstract. Accession No. 2000078574, available from STN Online on 02/0400.

Hoet, Peter H.M. et al., "Nanoparticles–known and unknown health risks," Journal of Nanobiotechnology, vol. 2, pp. 1–15, 2004.

Borm, Paul J. A. et al., "Toxicological hazards of inhaled nanoparticles–potential implications for drug delivery, " Journal of Nanoscience and Nanotechology, vol. 4(5), pp. 521–531, 2004.

Ozkan, M., "Quantum dots and other nanoparticles: what can they offer to drug discovery"? Drug Discovery Today, vol. 9(24), pp. 1065–1071, 2004.

Williams, D., "Nanocrystalline metals: another opportunity for medical devices?" Medical Device Technology, vol. 14(9), p. 12 (pp. 1–4 in the copy obtained via ProQuest), 2003.

Grier, N., Ph.D., "Silver and its Compounds", Disinfection, Sterilization and Preservation, pp. 395–407, 1977. (S.S. Block, Lea and Febiger).

* cited by examiner

TREATMENT OF MUCOSAL MEMBRANES

CROSS-REFERENCE TO RELATED APPLICATIONS

This application is a Continuation-in-Part of co-pending U.S. patent application Ser. No. 09/840,637 filed Apr. 23, 2001. This application also claims priority from U.S. Provisional Patent Application No. 60/285,884, filed Apr. 23, 2001. To the extent that they are consistent herewith, the aforementioned applications are incorporated herein by reference.

FIELD OF THE INVENTION

The invention relates to the use of antimicrobial or noble metals for administration to mucosal membranes.

BACKGROUND OF THE INVENTION

Mucosal membranes are the epithelial membranes which line the oral cavity, the nasal, bronchial, pulmonary, trachea and pharynx airways, the otic and ophthalmic surfaces, the urogenital system, including the prostate, the reproductive system and the gastrointestinal tract including the colon and rectal surfaces. Mucosal membrane includes the surface membranes or cell structures of the mucosal membrane at a subject's targeted site. Mucosal membranes represent the first portal of entry for many diseases. Exemplary of important pathogens of viral (RNA or DNA viruses), bacterial (gram positive and gram negative, whether aerobic, facultative, or anaerobic), fungal, or algal origin (all of which are exemplary of sources of microbial infection of the mucosal membranes) are: *Vibrio cholerae,* enterotoxigenic *Escherichia coli,* Rotavirus, *Clostridium difficile, Shigella* species, *Salmonella typhi,* parainfluenza virus, influenza virus, *Streptococcus pneumoniae, Borellia burgdorferi,* HIV, *Streptococcus mutans, Plasmodium falciparum, Staphylococcus aureus, Pseudomonas aeruginosa,* rabies virus, Epstein-Barr virus, Herpes simplex virus, type I and II.

Mucosal membranes are also the subject of many disorders and diseases which are not strictly microbial in nature, for instance cystic fibrosis, prostatitis and digestive disorders.

Particular problems arise in treating patients suffering from microbial infections, disorders or diseases of the mucosal membrane when the patient is allergic to a form of treatment such as an allergy to all or particular antibiotics.

In general, additional therapies for infections, diseases or disorders of the mucosal membranes are still needed.

SUMMARY OF THE INVENTION

Methods of introducing atomic disorder into antimicrobial metals are taught by Burrell et al, in WO 93/23092, published Nov. 25, 1993, WO 95/13704, published May 26, 1995, and WO 9841095 published Sep. 24, 1998. Through research, the inventors have established that crystalline antimicrobial metals such as silver, formed with atomic disorder, are effective and safe antimicrobial agents against the microbes associated with infections of mucosal membranes. The inventors have further established through clinical observations, and in animal experiments, that antimicrobial or noble metals such as silver, formed with atomic disorder, reduce inflammation of mucosal membranes. This research has resulted in a new therapeutic treatment of mucosal membranes. This new treatment has advantages of fewer side effects, use for patients who cannot be treated with other antibiotics, and less chance of development of resistant bacteria. The antimicrobial metal is preferably formed with atomic disorder at the nanocrystalline level, that is with a very fine, nanocrystalline grain size.

Without being bound by the same, it is believed that the nanocrystalline antimicrobial metals formed with atomic disorder are capable of releasing highly active clusters of the antimicrobial metal (example clusters of $Ag^0$ or $Ag^+/Ag^0$), which are responsible for the surprisingly enhanced antimicrobial activity and the surprising presence of the anti-inflammatory activity in the treatment of mucosal membranes, compared with other known antimicrobials such as silver salts (ex. silver nitrate), silver zeolites which release only $Ag^+$, or silver metal and silver oxide which have only minor solubility. Clusters are known to be small groups of atoms, ions or the like, as described by R. P. Andres et al., "Research Opportunities on Cluster and Cluster-Assembled Materials", J. Mater. Res. Vol 4, No 3, 1989, p. 704. For silver, clusters are believed to contain less than the 14 atoms of a normal face centered cubic crystal lattice form of silver.

The invention thus may be used to deliver nanocrystalline antimicrobial or, more preferably, noble metals formed with atomic disorder across mucosal membranes including without limitation gastrointestinal epithelial tissue, lung epithelial tissue and other mucosal surfaces including oral surfaces, nasal surfaces, sinus surfaces, pharynx surfaces, tracheal surfaces, esophageal surfaces, vaginal surfaces, rectal surfaces, colon surfaces, otic and ophthalmic surfaces, The invention also provides treatment for respiratory disorders, whether infectious, inflammatory or immunologic in origin, including without limitation emphysema, chronic bronchitis, asthma, pulmonary edema, acute respiratory distress syndrome, bronchopulmonary dysplasia, pulmonary fibrosis, pulmonary atelectasis, tuberculosis, pneumonia and cystic fibrosis, with the use of aerosols, mists or sprays of the nanocrystalline antimicrobial metals.

The invention also provides treatment for other disorders of mucosal membranes, including without limitation, prostatitis, sinusitis, digestive disorders, TENS (toxic epidermal necrolysis syndrome), Stevens Johnstone Syndrome, cystic fibrosis, bronchitis, pneumonia, pharyngitis, common cold, ear infection, sore throat, STD's (sexually transmitted diseases such as syphilis, gonorrhea, herpes, genital warts, HIV, and chlamydia), inflammatory bowel disease, colitis, hemorrhoids, thrush, dental, oral and periodontal disease such as gingivitis, dental caries, periodental inflammation and malodour.

Methods and formulations of this invention have application to both humans and animals.

One particularly preferred embodiment of the invention involves the treatment of respiratory disorders by the administration of the antimicrobial or noble metal as an aerosol, mist or spray, which can be generated by a nebulizer, or by delivering powders or solutions of the metal by inhalers. Another particularly preferred embodiment is the administration of the antimicrobial or noble metal as an instillation for such disorders as inflammatory bowel disease. The antimicrobial or noble metal may be administered alone, or with a carrier such as saline solutions, DMSO, an alcohol or water, most preferably water. An effective daily amount of the antimicrobial or noble metal will vary with the subject, but will be less than is toxic while still providing a therapeutic effect. An exemplary dose is from about 10 μg/kg to about 50 mg/kg of body weight, more preferably 0.5–10 mg/kg.

The inventors have thus discovered that antimicrobial metals, preferably selected from one or more of silver, gold, platinum and palladium, are effective in the treatment of the mucosal membranes. These antimicrobial metals are formed with atomic disorder, such that ions, clusters, atoms or molecules of the metals are released at a concentration sufficient to provide a localized antimicrobial and anti-inflammatory effect. Most preferably, the antimicrobial or noble metals are in a nanocrystalline form, and include sufficient atomic disorder to provide an antimicrobial and anti-inflammatory effect on a sustainable basis.

The crystalline forms of these antimicrobial or noble metals may be used in, or formulated from, any of the following formats:

1. Coatings of the antimicrobial metals on medical grade substrates, for example, dressings, packings, meshes, films, filtering surfaces, filters, infusers, fibres such as dental floss or sutures, containers or vials, from materials composed of, for example, polyethylene, high density polyethylene, polyvinylchloride, latex, silicone, cotton, rayon, polyester, nylon, cellulose, acetate, carboxymethylcellulose, alginate, chitin, chitosan and hydrofibres;
2. Powders, preferably prepared as powders of the antimicrobial or noble metals (i.e., as free standing powders), or as coatings of the antimicrobial or noble metals on biocompatible substrates in powder form, preferably on hydrocolloids, bioabsorbable and/or hygroscopic substrates such as:

Synthetic Bioabsorbable Polymers: for example polyesters/polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers, or Naturally Derived Polymers:

Proteins: albumin, fibrin, collagen, elastin;

Polysaccharides: chitosan, alginates, hyaluronic acid; and

Biosynthetic Polyesters: 3-hydroxybutyrate polymers;

3. Occlusions or hydrated dressings, in which the dressing is impregnated with a powder or solution of the antimicrobial metals, or is used with a topical formulation of the antimicrobial metals, with such dressings for example as hydrocolloids, hydrogels, polyethylene, polyurethane, polvinylidine, siloxane or silicone dressings
4. Gels, formulated with powders or solutions of the antimicrobial or noble metals with such materials as hydrocolloid powders such as carboxymethylcellulose, alginate, chitin, chitosan and hydrofibres, together with such ingredients as preservatives, pectin and viscosity enhancers;
5. Creams, lotions, pastes, foams and ointments formulated with powders or solutions of the antimicrobial or noble metals, for example as emulsions or with drying emollients;
6. Liquids, formulated as solutions, dispersions, or suspensions, by dissolving coatings or powders of the antimicrobial or noble metals, for example as topical solutions, aerosols, mists, sprays, drops, infusions and instillation solutions for body cavities and tubes such as the bladder, prostate, perintheal, pericharcliar, pleural, intestinal and ailimentary canal;
7. Formulations suitable for administration to the nasal membranes, the oral cavity or to the gastrointestinal tract, formulated with powders or liquids of the antimicrobial or noble metal in such forms as lozenges, toothpastes, gels, powders, coated dental implants, dental floss or tape, chewing gum, wafers, mouth washes or rinses, drops, sprays, elixirs, syrups, tablets, or capsules;
8. Formulations suitable for vaginal or rectal administration formulated with powders or liquids of the antimicrobial or noble metal in such forms as suppositories, dressings, packings, tampons, creams, gels, ointments, pastes, foams, sprays, and solutions for retention enemas or instillations.

Solutions of the antimicrobial or noble metals may lose some activity with aging and are thus either stabilized or generated fresh for administration. Alternatively, the antimicrobial or noble metals may be packaged for convenient solution generation, for instance in a pervious membrane such as a tea bag-type infusers. Other two part systems or two phase may be used in which the metal coating or powder is separated from any liquid carrier or hydrating agents, for example packaging the components in kit form, with the antimicrobial metal being provided in dissolving capsules, as a coating on the inside of vials or containers, on substrates such as dressings, separated by a membrane which can be perforated, or in a separate container from the carrier etc.

In the above formats, the antimicrobial or noble metals are thus formulated from coatings or powders of the antimicrobial or noble metals, or from solutions prepared by dissolving the coatings or powders therein. The formulations include a therapeutically effective amount of the coatings or powders, and most preferably, the following amounts:

| | |
|---|---|
| For coatings: | 150–3000 nm thick coatings for substrates, or thicker for forming powders (such coatings can be used to generate 0.001 to 10% by weight solutions) |
| For gels, creams etc.: | 0.01–30% by weight, more preferably 0.01–10% by weight and most preferably 0.1–5% by weight of the antimicrobial or noble metal powder |
| For liquids: | 0.001–10% by weight, more preferably 0.01 to 5% by weight and most preferably 0.1 to 1% by weight of the antimicrobial or noble metal (generated from any format, including coatings, flakes, powders). |

Concentrations of the antimicrobial or noble metal species in solution will vary according to the application, formulation and subject, but will generally range from 1–5000 μg/ml, more preferably 20–3000 μg/ml, more preferably 40–800 μg/ml, and most preferably 50–500 μg/ml.

Nanocrystalline coatings of the antimicrobial or noble metals are most preferably deposited onto substrates such as dressings, for example one or more layers of medical dressing materials which can be laminated with uncoated layers of medical dressing materials. The coatings can be prepared by known techniques for preparing nanocrystalline coatings, but are most preferably prepared by physical vapour deposition under conditions which create atomic disorder. The nanocrystalline coatings may be prepared to create an interference colour so as to provide an indicator, as described in prior patent application WO 98/41095, published Sep. 24, 1998, and naming inventors R. E. Burrell and R. J. Precht.

Nanocrystalline powders of the antimicrobial or noble metals may be prepared as nanocrystalline coatings preferably of the above thickness, on powdered substrates such as chitin, or may be prepared as nanocrystalline coatings on a substrate such as a silicon wafer, and then scraped off as a nanocrystalline powder. Alternatively, fine grained or nanocrystalline powders of the antimicrobial or noble metals may be cold worked to impart atomic disorder, as disclosed in prior patent application WO 93/23092, published Nov. 25, 1993, naming Burrell et al., as inventors.

Thus, the invention broadly provides a method of reducing inflammation or infection of a mucosal membrane, comprising contacting a problem area of the mucosal membrane with a therapeutically effective amount of one or more antimicrobial metals in a crystalline form to provide a localized anti-inflammatory effect, wherein the one or more antimicrobial metals are characterized by sufficient atomic disorder, such that the metal, in contact with an alcohol or water-based electrolyte, releases atoms, ions, molecules, or clusters of at least one antimicrobial metal at a concentration sufficient to provide a localized anti-inflammatory effect.

In another broad aspect of the invention, there is provides a method of reducing inflammation or infection of a mucosal membrane comprising:

a) providing a therapeutically effective amount of one or more antimicrobial metals in a crystalline form characterized by sufficient atomic disorder such that the metal, in contact with an alcohol or water-based electrolyte, releases atoms, ions, molecules, or clusters of at least one antimicrobial metal at a concentration sufficient to provide a localized anti-inflammatory effect.

b) providing a water or alcohol-based electrolyte;

c) bringing a) into contact with b) so as to provide dissolution of the one or more antimicrobial metals; and d) maintaining or applying the mixture from c) in contact with an area of infection or inflammation of the mucosal membrane to provide an antimicrobial or anti-inflammatory effect.

In yet another broad aspect, the invention provides a kit for reducing inflammation or infection of a mucosal membrane comprising a therapeutically effective amount of one or more antimicrobial metals in a crystalline form characterized by sufficient atomic disorder such that the metal, in contact with an alcohol or water-based electrolyte, releases atoms, ions, molecules, or clusters of at least one antimicrobial metal, the one or more antimicrobial metals being provided in a dosage form to provide a localized anti-inflammatory effect to the mucosal membrane.

As used herein and in the claims, the terms and phrases set out below have the meanings which follow.

"Metal" or "metals" includes one or more metals whether in the form of substantially pure metals, alloys or compounds such as oxides, nitrides, borides, sulphides, halides or hydrides.

"Antimicrobial metals" are silver, gold, platinum, palladium, iridium, zinc, copper, tin, antimony, bismuth, or mixtures of these metals with same or other metals, silver, gold, platinum and palladium being preferred, and silver being most preferred.

"Noble metals" are silver, gold, platinum and palladium, or mixtures of such metals with same or other metals, with silver metal being the most preferred.

"Antimicrobial effect" means that atoms, ions, molecules or clusters of the antimicrobial or noble metal are released into the electrolyte which the coating contacts in concentration sufficient to inhibit microbial growth on and in the vicinity of the coating. The most common methods of measuring an antimicrobial effect are a zone of inhibition test (which indicates an inhibitory effect, whether microbiostatic or microbiocidal) or a logarithmic reduction test (which indicates a microbiocidal effect). In a zone of inhibition test (ZOI) the material to be tested is placed on a bacterial lawn (or a lawn of other microbial species) and incubated. A relatively small or no ZOI (ex. less than 1 mm) indicates a non-useful antimicrobial effect, while a larger ZOI (ex. greater than 5 mm) indicates a highly useful antimicrobial effect. The ZOI is generally reported as a corrected zone of inhibition (CZOI), wherein the size of the test sample is subtracted from the zone. A logarithmic reduction test in viable bacteria is a quantitative measure of the efficacy of an antibacterial treatment; for example, a 5 log reduction means a reduction in the number of microorganisms by 100,000-fold (e.g., if a product contained 100,000 pertinent microorganisms, a 5 log reduction would reduce the number of pertinent microorganisms to 1). Generally, a 3 log reduction represents a bactericidal effect. The logarithmic reduction test involves combining an inoculum of bacteria or other microbial species with the test treatment, incubating the inoculum with the test treatment, recovering the bacteria or other microbial species, and enumerating the bacteria or other microbial species using serial dilutions. Examples of these tests are set out in the examples which follow.

"Anti-inflammatory effect" means a reduction in one ore more of the symptoms of erythema (redness), edema (swelling), pain and pruritus which are characteristic of inflammatory conditions of mucosal membranes.

"Biocompatible" means generating no significant undesirable host response for the intended utility. Most preferably, biocompatible materials are non-toxic for the intended utility. Thus, for human utility, biocompatible is most preferably non-toxic to humans or human tissues.

"Sustained release" or "sustainable basis" are used to define release of atoms, molecules, ions or clusters of an antimicrobial metal that continues over time measured in hours or days, and thus distinguishes release of such metal species from the bulk metal, which release such species at a rate and concentration which is too low to be therapeutically effective, and from highly soluble salts of antimicrobial metals such as silver nitrate, which releases silver ions virtually instantly, but not continuously, in contact with an alcohol or electrolyte.

"Atomic disorder" includes high concentrations of one or more of: point defects in a crystal lattice, vacancies, line defects such as dislocations, interstitial atoms, amorphous regions, grain and sub grain boundaries and the like relative to its normal ordered crystalline state. Atomic disorder leads to irregularities in surface topography and inhomogeneities in the structure on a nanometer scale.

"Normal ordered crystalline state" means the crystallinity normally found in bulk metal materials, alloys or compounds formed as cast, wrought or plated metal products. Such materials contain only low concentrations of such atomic defects as vacancies, grain boundaries and dislocations.

"Diffusion", when used to describe conditions which limit diffusion in processes to create and retain atomic disorder, i.e. which freeze-in atomic disorder, means diffusion of atoms (adatom diffusion) and/or molecules on the surface or in the matrix of the material being formed.

"Alcohol or water-based electrolyte" is meant to include any alcohol or water-based electrolyte that the antimicrobial materials of the present invention might contact in order to activate (i.e. cause the release of species of the antimicrobial metal) into same. The term is meant to include alcohols (short chain ($C_6$ or less) and preferably $C_4$ or less), water, gels, fluids, solvents, and tissues containing, secreting or exuding water or water-based electrolytes, including body fluids (for example blood, urine or saliva), and body tissue (for example mucosal membranes).

"Bioabsorbable" as used herein in association includes substrates which are useful in medical devices, that is which are biocompatible, and which are capable of bioabsorption in period of time ranging from hours to years, depending on the particular application.

"Bioabsorption" means the disappearance of materials from their initial application site in the body (human or mammalian) with or without degradation of the dispersed polymer molecules.

"Colour change" is meant to include changes of intensity of light under monochromatic light as well as changes of hue from white light containing more than one wavelength.

An "interference colour" is produced when light impinges on two or more partly reflective surfaces separated by a distance which bears the right relationship to the wavelength of the light to be removed by destructive interference.

"Partly reflective" when used to describe the base or top layer materials, means that the material has a surface which reflects a portion of incident light, but which also transmits a portion of the incident light. Reflection occurs when a ray of incoming light encounters a boundary or interface characterized by a change in refractive index between two media. For the top layer of the antimicrobial materials of this invention, that interface is with air. For the base layer, the interface is with the top layer. The reflectance of the base and top layers is balanced so as to generate an interference colour.

"Partly light transmissive" when used to describe a thin film of the top layer material means that the thin film is capable of transmitting at least a portion of incident visible light through the thin film.

"Detectable" when used to describe a colour change means an observable shift in the dominant wavelength of the reflected light, whether the change is detected by instrument, such as a spectrophotometer, or by the human eye. The dominant wavelength is the wavelength responsible for the colour being observed.

"Cold working" as used herein indicates that the material has been mechanically worked such as by milling, grinding, hammering, mortar and pestle or compressing, at temperatures lower than the recrystallization temperature of the material. This ensures that atomic disorder imparted through working is retained in the material.

"Pharmaceutically- or therapeutically-acceptable" is used herein to denote a substance which does not significantly interfere with the effectiveness or the biological activity of the active ingredients (antimicrobial and anti-inflammatory activities) and which is not toxic or has an acceptable toxic profile to the host to which it is administered.

"Therapeutically effective amount" is used herein to denote any amount of a formulation of the antimicrobial or noble metals which will exhibit either or both of an antimicrobial and optionally an anti-inflammatory effect, when applied to the affected area of the mucosal membrane. A single application of the formulations of the present invention may be sufficient, or the formulations may be applied repeatedly over a period of time, such as several times a day for a period of days or weeks. The amount of the active ingredient, that is the antimicrobial or noble metal in the form of a coating, powder or dissolved in liquid solution, will vary with the conditions being treated, the stage of advancement of the condition, the age and type of host, and the type and concentration of the formulation being applied. Appropriate amounts in any given instance will be readily apparent to those skilled in the art or capable of determination by routine experimentation.

"Carrier" means a suitable vehicle including one or more solid, semisolid or liquid diluents, excipients or encapsulating substances which are suitable for administration to the mucosal membrane.

"Nanocrystalline" is used herein to denote single-phase or multi-phase polycrystals, the grain size of which is less than about 100, more preferably <50, even more preferably <40, even more preferably <30, and most preferably <25 nanometers in at least one dimension. The term, as applied to the crystallite or grain size in the crystal lattice of coatings, powders or flakes of the antimicrobial or noble metals, is not meant to restrict the particle size of the materials when used in a powder form.

"Powder" is used herein to include particulates of the antimicrobial or noble metals ranging from nanocrystalline (less than 100 nm) to submicron sized powders up to flakes. Preferably, powders of the antimicrobial or noble metals used in the present invention are sized at less than 100 μm, and more preferably less than 40 μm, and most preferably less than 10 μm.

"Grain size", or "crystallite size" means the size of the largest dimension of the crystals in the antimicrobial metal coating or powder.

"Hydrocolloid" means a synthetically prepared or naturally occurring polymer capable of forming a thickened gel in the presence of water and polyols (swelling agent). The swelling agent must be capable of swelling the hydrocolloid chosen in order to form the gel phase.

"Hydrogels" means a hydrocolloid swollen with water or another hydrophilic liquid which is used for absorbing or retaining moisture or water.

"Gel" means a composition that is of suitable viscosity for such purposes, e.g., a composition that is of a viscosity that enables it to be applied and remain on a substrate or the mucosal membrane.

"Mucosal membrane" includes the epithelial membranes which line the oral cavity, the nasal, bronchial, pulmonary, trachea and pharynx airways, the otic and ophthalmic surfaces, the urogenital system, including the prostate, the reproductive system and the gastrointestinal tract, including the colon and rectal surfaces. Reference to mucosal membrane herein is meant to include the surface membranes or cell structures of the mucosal membrane at a targeted site.

"Diseases or conditions of the oral cavity" means diseases or conditions of the oral cavity whether infectious, inflammatory or immunologic in origin, including without limitation periodontal disease, gingivitis, periodontitis, periodontosis, inflammatory conditions of the tissues within the oral cavity, caries, necrotizing ulcerative gingivitis, oral or breath malodor, herpetic lesions, infections following dental procedures such as osseous surgery, tooth extraction, periodontal flap surgery, dental implantation, scaling and root planing, dentoalveolar infections, dental abscesses (e.g., cellulitis of the jaw; osteomyelitis of the jaw), acute necrotizing ulcerative gingivitis, infectious stomatitis (i.e., acute inflammation of the buccal mucosa), Noma (i.e., gangrenous stomatitis or cancrum oris), sore throat, pharyngitis, and thrush.

"Respiratory disorders" means respiratory disorders of the nasal, bronchial, pulmonary, trachea and pharynx airways whether infectious, inflammatory or immunologic in origin, including without limitation emphysema, chronic bronchitis, asthma, pulmonary edema, acute respiratory distress syndrome, bronchopulmonary dysplasia, pulmonary fibrosis, pulmonary atelectasis, tuberculosis, pneumonia, TENS, Stevens Johnstone Syndrome, common cold, sore throat, pharyngitis, and cystic fibrosis.

"Gastrointestinal disorders" means disorders of the gastrointestinal tract whether infectious, inflammatory or immunologic in origin, including without limitation, digestive ulcers such as esophageal ulcer, gastric ulcer and duodenal ulcer, and also esophagitis, gastritis, enteritis, enterogastric intestinal hemorrhage, colitis, inflammatory bowel disease, and hemorrhoids.

"Nasal disorders" means disorders of the nasal passages whether infectious, inflammatory or immunologic in origin, including without limitation sinusitis.

"Disorders of the urogenital and reproductive systems" means disorders of these systems whether infectious, inflammatory or immunologic in origin, including without limitation STD's, HIV, chlamydia, syphilis, gonorrhea, Herpes, genital warts, and prostatitis.

When used herein and in the claims, the term "nanocrystalline antimicrobial metal" and similar terminology such as "nanocrystalline coating or powder" is meant to refer to antimicrobial metal, coating or powder formed with atomic disorder and having a nanocrystalline grain size.

DESCRIPTION OF THE PREFERRED EMBODIMENTS

Crystalline forms of the antimicrobial metal or noble metals can be prepared as coatings or powders, or as liquids prepared by dissolving the coatings or powders. The crystalline coatings or powders are most preferably formed with atomic disorder in accordance with the techniques published in the prior patent applications of Burrell et al., see for example WO 93/23092, published Nov. 25, 1993, WO 95/13704, published May 26, 1995 and WO 98/41095, published Sep. 24, 1998.

Pharmaceutical formulations for treatment of mucosal membranes utilize the antimicrobial or noble metals in powder, coatings or solution form. Preparation of the antimicrobial or noble metals as powders or coatings is set out below in section A, format for formulations are set forth in section B, sterilization in section C, and formulating, dosages and treatment are set forth in section D.

A. Preparation of Crystalline Forms of the Antimicrobial Metals with Atomic Disorder a) Antimicrobial Metal Coatings on Dressings or other Substrates Dressings or other substrates such as packings, vials, fabric, fibres, liners, mesh, filtering surfaces etc. may be coated with antimicrobial coatings formed with atomic disorder. The description below is directed to coatings on dressing materials, but the coating techniques are equally applicable to coating other substrates. Dressings coated with antimicrobial metals in accordance with the invention include one or more layers of medical dressing materials. Multiple layers may be laminated together by known means such as low temperature thermal fusing, stitching or, most preferably, ultrasonic welding.

The dressing may be formed to include an occlusive or semi-occlusive layer such as an adhesive tape or polyurethane film in order to secure the dressing in place, and retain moisture for release of ions, atoms, molecules or clusters of the antimicrobial metal (hereinafter antimicrobial metal species).

The preferred and alternate compositions of the dressing layers, together with the preferred nanocrystalline antimicrobial metal coatings, are set out in further detail below.

i) Dressing Materials

The dressing is formed of a perforated, preferably non-adherent material which allows for fluids to penetrate or diffuse there through in either or both directions. The perforated material may be formed of a woven or non-woven, non-woven being preferred, fabric such as cotton, gauze, a polymeric net or mesh such as polyethylene, nylon, polypropylene or polyester, an elastomer such as polyurethane or polybutadiene elastomers, or a foam such as open cell polyurethane foam. Exemplary perforated, non-adherent materials useful for the dressing include non-woven meshes such as DELNET™ P530, which is a non-woven veil formed of high density polyethylene using extrusion, embossing and orientation processes, produced by Applied Extrusion Technologies, Inc. Of Middletown, Del., USA. This same product is available as Exu-Dry CONFORMANT 2™ Wound Veil, from Frass Survival Systems, Inc., Bronx, N.Y., USA as a subset of that company's Wound Dressing Roll (Non-Adherent) products. Other useful non-woven meshes include CARELLE™ or NYLON 90™, available from Carolina Formed Fabrics Corp., N-TERFACE™, available from Winfield Laboratories, Inc., of Richardson, Tex., USA. Exemplary woven meshes may be formed from fibreglass or acetate, or cotton gauze. An exemplary hydrophilic polyurethane foam is HYPOL™, available from W. R. Grace & Co., New York, N.Y., USA.

For ease of ultrasonic welding for lamination, at least one dressing layer is preferably formed from a polymeric material which is amenable to ultrasonic welding, that is which will melt on the application of localized heat and then fuse multiple layers together on cooling.

If desired, a second, absorbent layer is formed from an absorbent material for holding sufficient moisture next to the mucosal membrane in order to activate the antimicrobial metal coating, that is to cause release of ions, molecules, atoms or clusters of the antimicrobial metal in order to cause an antimicrobial and anti-inflammatory effect. Preferably, the absorbent material is an absorbent needle punched non-woven rayon/polyester core such as SONTARA™ 8411, a 70/30 rayon/polyester blend commercially available from Dupont Canada, Mississauga, Ontario, Canada. This product is sold by National Patent Medical as an American White Cross sterile gauze pad. However, other suitable absorbent materials include woven or non-woven materials, non-woven being preferred made from fibers such as rayon, polyester, rayon/polyester, polyester/cotton, cotton and cellulosic fibers. Exemplary are creped cellulose wadding, an air felt of air laid pulp fibers, cotton, gauze, and other well known absorbent materials suitable for medical dressings.

A third layer of the dressing, if used, is preferably formed of perforated, non-adherent material such as used in the first layer. This allows moisture penetration as sterile water and the like are added in order to activate the antimicrobial metal coating.

Additional layers may be included between or above the first, second and third layers as is well known in medical dressings. The coated dressing layers may be combined with an adhesive layer, in a well known manner.

The dressing may be used as a single layer, or may be used as multiple layers laminated together at intermittent spaced locations across the dressing by ultrasonic welds. Ultrasonic welding is a known technique in the quilting art. Briefly, heat (generated ultrasonically) and pressure are applied to either side of the dressing at localized spots through an ultrasonic horn so as to cause flowing of at least one of the plastic materials in the first and second layers and the subsequent bonding together of the layers on cooling. The welds appear at localized circular spots and are preferably less than 0.5 cm in diameter.

The use of ultrasonic welding of the layers at spaced locations has the advantage of retaining the absorbent and moisture penetration properties of the dressing layers, while retaining the conforming properties of the dressing. Edge seams, stitching and adhesives have the disadvantage of interfering with one or more of these desirable properties of the dressings. Furthermore, by spacing the welds at intermittent locations across the dressing, the dressing may be cut to smaller sizes, as needed, without causing delamination. Preferred spacings of about 2.5 cm between welds allows the dressing to be cut down to about 2.5 cm sizes, while maintaining at least one weld to hold the laminated layers together.

ii) Nanocrystalline Coatings of Antimicrobial Metals

The coated substrate, for example a dressing, preferably includes a nanocrystalline coating of one or more of the antimicrobial metals. The coating is applied to one or more of the dressing layers, but is most preferably applied at least to the mucosal membrane facing layer.

The nanocrystalline coating is most preferably formed with atomic disorder in accordance with the procedures set out above and as described in WO 93/23092, WO 95/13704, and WO 098/41095, and as set out below. Most preferably, the coating is formed as a multilayer coating of the antimicrobial metals, having a top and a base layer, as set below, to produce an interference colour. In this way, the coating provides not only the active ingredient for the treatment of mucosal membranes, but also acts as an indicator of activation of the dressing. As the top layer of the coating is activated with an alcohol or water-based electrolyte, such as sterile water or ethanol, even minor dissolution of the antimicrobial metal results in a detectable colour change, indicating that the coating has been activated. If there is no colour change, additional moisture might be provided to the dressing by adding water, until a colour change is detected. Once activated, the dressing should be maintained in a moist condition, for example by the addition of sterile water, if necessary.

iii) Multilayer Nanocrystalline Coatings of Antimicrobial Metals with Interference Colour The coated substrates, for example dressings may include the antimicrobial metal coating formed with at least two metal layers, a base layer and a top layer over the base layer, so as to produce an interference colour, as set forth in WO 98/41095, the teachings of which are incorporated herewith by reference. The indicator colour can function as an indicator when contacted with a water or alcohol-based electrolyte, since the coating will change colour. An exemplary multilayer nanocrystalline coating of silver with a blue interference colour is set forth in Example 1.

iv) Nanocrystalline Coatings of Antimicrobial Metals Containing Atomic Disorder

The coatings of the present invention are formed in a crystalline form from one or more antimicrobial metals with atomic disorder. The production of atomic disorder through physical vapour deposition techniques is described in WO 93/23092 and WO 95/13704, and as outlined below.

The antimicrobial metal is deposited as a thin metallic film on one or more surfaces of the dressing by vapour deposition techniques. Physical vapour techniques, which are well known in the art, all deposit the metal from the vapour, generally atom by atom, onto a substrate surface. The techniques include vacuum or arc evaporation, sputtering, magnetron sputtering and ion plating. The deposition is conducted in a manner to create atomic disorder in the coating as defined above. Various conditions responsible for producing atomic disorder are useful. These conditions are generally those which one has been taught to avoid in thin film deposition techniques, since the object of most thin film depositions is to create a defect free, smooth and dense film (see for example J. A. Thornton, "Influence of Apparatus Geometry and Deposition Conditions on the Structure and Topography of Thick Sputtered Coatings," J. Vac. Sci. Technol., 11(4), 666–670, 1974).

The preferred conditions which are used to create atomic disorder during the deposition process include:

a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3; and optionally one or both of:

a higher than normal working gas pressure (or ambient pressure in depositions not using a working gas), i.e. for vacuum evaporation: e-beam or arc evaporation, greater than 0.001 Pa (0.01 mT), gas scattering evaporation (pressure plating) or reactive arc evaporation, greater than 2.67 Pa (20 mT); for sputtering: greater than 10 Pa (75 mT); for magnetron sputtering: greater than about 1.33 Pa (10 mT); and for ion plating: greater than about 26.67 Pa (200 mT); and maintaining the angle of incidence of the coating flux on the surface to be coated at less than about 75°, and preferably less than about 30°.

For economic reasons, the thin metal film has a thickness no greater than that needed to provide release of antimicrobial metal species on a sustainable basis over a suitable period of time, and to generate the desired interference colour. Within the preferred ranges of thicknesses set out above, the thickness will vary with the particular metal in the coating (which varies the solubility and abrasion resistance), and with the degree of atomic disorder in (and thus the solubility of) the coating. The thickness will be thin enough that the coating does not interfere with the dimensional tolerances or flexibility of the device for its intended utility.

The therapeutic effect of the material so produced is achieved when the coating is brought into contact with an alcohol or a water-based electrolyte, thus releasing metal ions, atoms, molecules or clusters. The concentration of the metal species which is needed to produce a therapeutic effect will vary from metal to metal.

The ability to achieve release of metal atoms, ions, molecules or clusters on a sustainable basis from a coating is dictated by a number of factors, including coating characteristics such as composition, structure, solubility and thickness, and the nature of the environment in which the device is used. As the level of atomic disorder is increased, the amount of metal species released per unit time increases. For instance, a silver metal film deposited by magnetron sputtering at $T/Tm < 0.5$ and a working gas pressure of about 0.93 Pa (7 mT) releases approximately ⅓ of the silver ions that a film deposited under similar conditions, but at 4 Pa (30 mT), will release over 10 days. Films that are created with an intermediate structure (ex. lower pressure, lower angle of incidence etc.) have Ag release values intermediate to these values as determined by bioassays. This then provides a method for producing controlled release metallic coatings. Slow release coatings are prepared such that the degree of disorder is low while fast release coatings are prepared such that the degree of disorder is high.

For continuous, uniform coatings, the time required for total dissolution will be a function of film thickness and the nature of the environment to which they are exposed. The relationship in respect of thickness is approximately linear, i.e. a two fold increase in film thickness will result in about a two fold increase in longevity.

It is also possible to control the metal release from a coating by forming a thin film coating with a modulated structure. For instance, a coating deposited by magnetron sputtering such that the working gas pressure was low (ex. 2 Pa or 15 mT) for 50% of the deposition time and high (ex. 4 Pa or 30 mTorr) for the remaining time, has a rapid initial release of metal ions, followed by a longer period of slow release. This type of coating is extremely effective on devices such as urinary catheters for which an initial rapid release is required to achieve immediate antimicrobial concentrations followed by a lower release rate to sustain the concentration of metal ions over a period of weeks.

The substrate temperature used during vapour deposition should not be so low that annealing or recrystallization of the coating takes place as the coating warms to ambient temperatures or the temperatures at which it is to be used (ex. body temperature). This allowable ΔT, that the temperature differential between the substrate temperature during deposition and the ultimate temperature of use, will vary from metal to metal. For the most preferred metal, Ag, preferred substrate temperatures of −20 to 200° C., more preferably −10° C. to 100° C. are used.

Atomic order may also be achieved, in either or both of the base and top layers by preparing composite metal materials, that is materials which contain one or more antimicrobial metals in a metal matrix which includes atoms or molecules different from the antimicrobial metals.

The preferred technique for preparing a composite material is to co- or sequentially deposit the antimicrobial metal(s) with one or more other inert, biocompatible metals selected from Ta, Ti, Nb, Zn, V, Hf, Mo, Si, Al and alloys of these metals or other metal elements, typically other transition metals. Such inert metals have a different atomic radii from that of the antimicrobial metals, which results in atomic disorder during deposition. Alloys of this kind can also serve to reduce atomic diffusion and thus stabilize the disordered structure. Thin film deposition equipment with multiple targets for the placement of each of the antimicrobial and biocompatible metals is preferably utilized. When layers are sequentially deposited the layer(s) of the biocompatible metal(s) should be discontinuous, for example as islands within the antimicrobial metal matrix. The final weight ratio of the antimicrobial metal(s) to biocompatible metal(s) should be greater than about 0.2. The most preferable biocompatible metals are Ti, Ta, Zn and Nb. It is also possible to form the antimicrobial coating from oxides, carbides, nitrides, sulphides, borides, halides or hydrides of one or more of the antimicrobial metals and/or one or more of the biocompatible metals to achieve the desired atomic disorder.

Another composite material may be formed by reactively co- or sequentially depositing, by physical vapour techniques, a reacted material into the thin film of the antimicrobial metal(s). The reacted material is an oxide, nitride, carbide, boride, sulphide, hydride or halide of the antimicrobial and/or biocompatible metal, formed in situ by injecting the appropriate reactants, or gases containing same, (ex. air, oxygen, water, nitrogen, hydrogen, boron, sulphur, halogens) into the deposition chamber. Atoms or molecules of these gases may also become absorbed or trapped in the metal film to create atomic disorder. The reactant may be continuously supplied during deposition for codeposition or it may be pulsed to provide for sequential deposition. The final weight ratio of reaction product to antimicrobial metal(s) should be greater than about 0.05. Air, oxygen, nitrogen and hydrogen are particularly preferred reactants, with oxygen being most preferred.

The above deposition techniques to prepare composite coatings may be used with or without the conditions of lower substrate temperatures, high working gas pressures and low angles of incidence previously discussed. One or more of these conditions are preferred to retain and enhance the amount of atomic disorder created in the coating.

The most preferred composite coatings are formed by sputtering silver, under conditions set out above, in an atmosphere containing oxygen, so as to form a coating of silver as a composite coating with oxygen.

Dressings coated with the antimicrobial coatings of this invention may be sterilized in the manner set out below.

b) Powders of Atomically Disordered Antimicrobial Metals

Crystalline powder forms of the antimicrobial or noble metals (particularly preferred being Ag, Au, Pt, and Pd) can be prepared as free standing powders, by coating powdered substrates, or from coatings on substrates which are then collected, for example by scraping, and then sized. The powders may be prepared as pure metals, metal alloys or compounds such as metal oxides or metal salts, by vapour deposition, mechanical working, or compressing to impart the atomic disorder. The crystalline powders are formed with atomic disorder in accordance with the techniques set out above and as published in the prior patent applications of Burrell et al., see for example WO 93/23092, published Nov. 25, 1993, and WO 95/13704, published May 26, 1995. The atomic disorder will most typically be formed in the metal powders during physical vapour deposition as set out above for coatings or by mechanically imparting the disorder, such as by milling, grinding, hammering, mortar and pestle or compressing, under conditions of low temperature (i.e., temperatures less than the temperature of recrystallization of the material) to ensure that annealing or recrystallization does not take place.

Alternatively, the powders may be formed by inert-gas condensation techniques, which are modified to provide atomic disorder in the powder produced, as taught in WO 95/13704 to Burrell et al.

Powders of the antimicrobial or noble metals are preferably formed by physical vapour deposition (PVD) onto a substrate such as a cold finger, a silicon wafer, solid plates, a rotating cylinder, a continuous belt in a roll coater, or on steel collectors in known PVD coaters. Preparation of powders of the present invention by sputtering onto a continuous belt in a roll coater, or other some other moving or rotating substrate surface is particularly advantageous, inasmuch as it can quickly and easily yield a relatively large supply of free-standing powder at a relatively low cost. A stainless steel belt can be used in the roll coating process without the need to provide additional cooling of the substrate. The powders or coatings and then are then scraped off to form a powder, and may be sized to avoid overly large particulates. The powders are scraped off the moving surface with scrapers which contact the moving surface at an angle sufficient to remove the coating in flake or powder form. The coating may be scraped off with scrapers angled for forward cutting of the coating from the moving surface, or with scrapers which remove the coating from the moving surface by reverse dragging action on the surface. The scrapers may be suspended above the belt, and either weighted or spring loaded to apply pressure sufficient to remove the coating from the moving surface. With a continuous belt, the scrapers can conveniently be located above the end rollers to remove the coating with a reverse dragging action as the belt rounds the end roller.

Alternatively, the powders of the antimicrobial or noble metals may be formed on powdered substrates which are biocompatible, or otherwise compatible for the end use of the powder. Particularly preferred powdered substrates are hydrocolloids, particularly those which are bioabsorbable and/or hygroscopic powders such as chitin. Exemplary bioabsorbable and/or hygroscopic powders are composed of:

Synthetic Bioabsorbable Polymers: for example polyesters/polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers.

Naturally Derived Polymers:
Proteins: albumin, fibrin, collagen, elastin;
Polysaccharides: chitosan, alginates, hyaluronic acid; and
Biosynthetic Polyesters: 3-hydroxybutyrate polymers.

The powders may be incorporated into or onto medical dressings or pharmaceutical formulations, by any methods known in the art. For example, the powders may be layered onto the substrates (dressings or powders), mechanically fixed within the fibres of the dressings, impregnated into dressings by physical blowing, or added to topical pharmaceutical ingredients.

Most preferably, powders of the present invention are sized at less than 100 μm, and more preferably less than 40 μm, and most preferably about 3–5 μm in size. For direct application to the mucosal membranes, powders are preferably sized less than 2 μm, and more preferably less than 1 μm.

The antimicrobial and anti-inflammatory effects of the nanocrystalline powder are achieved when the powder, is brought into contact with an alcohol or a water-based electrolyte, thus releasing the antimicrobial or noble metal ions, atoms, molecules or clusters.

B. Formulations for Administration to Mucosal Membranes

1. Coated Substrates coated with antimicrobial metals formed with atomic disorder are described above. These techniques can be used to coat dressings, meshes, films, filtering surfaces, filters, packings, fibres such as dental floss and sutures, the inside of vials or containers etc. The coated substrates in the form of dressings or packings etc., can be used directly on the affected area of the mucosal membrane, or they can be used to generate powders, liquid or other formulations as set out below.
2. Powders of the antimicrobial metals formed with atomic disorder are set out above, and may be used in that form directly on the affected area of the mucosal membrane, or in other formulations such as dressings, occlusions, creams, liquids etc. Alternatively, powders may be formulated within liquid pervious membranes such as filters, meshes and the like, such as a tea bag-type infuser, for generating liquids containing dissolved species of the antimicrobial metal.
3. Occlusions may include a hydrated dressing, with a sealing material overlaid on the outside, to the area of mucosal membrane to be treated. The term hydrated dressing is meant to include non-hydrated dressings which become hydrated upon contact with an alcohol or water-based electrolyte. Occlusion prevents loss of the therapeutic agent from the mucosal membrane, promotes hydration, and increases mucosal membrane temperature. Examples of hydrated dressings include hydrocolloids, hydrogels, polyethylene, polyurethane, polyvinylidine, and siloxane or silicone dressings. The hydrated dressing can either be impregnated with a solution or powder of the antimicrobial metals of this invention, or can be used with a topical formulation of the antimicrobial metals of this invention.

An exemplary occlusion is a hydrocolloid dressing impregnated with nanocrystalline silver. Alternatively, one might use a non-impregnated hydrocolloid dressing to occlude a nanocrystalline silver-containing gel placed on a problematic area of the mucosal membrane. A hydrocolloid is a synthetically prepared or naturally occurring polymer capable of forming a thickened gel in the presence of water and polyols (swelling agent). The swelling agent is a hydrophilic liquid capable of swelling the hydrocolloid chosen in order to form the gel phase. The hydrocolloid may be selected from the group comprising:

a) representative natural or synthetically modified polysaccharides (e.g., cellulose or its derivatives such as carboxymethylcellulose, hydroxypropylcellulose, methylcellulose, hydroxypropylmethylcellulose or hydroxyethylcellulose, starch, glycogen, gelatin, pectin, chitosan and chitin; and
b) representative gums from algal extracts, seed extracts, or plant exudates (e.g., gum arabic, locust bean gum, karaya gum, gum tragacanth, ghatti gum, agar-agar, carrageenans, alginates, carob gum, guar gum, xanthan gum); and
c) synthetic polymers which may be either linear or crosslinked (e.g. polymers prepared from N-vinyl lactams, e.g. N-vinyl-2-pyrrolidone, 5-methyl-N-vinyl-2-pyrrolidone).

The hydrocolloid is present in an amount of from about 0.1% to 20% of the weight and preferably 1% to 10%. The hydrocolloid can range for example, from 1 to 10% of the total weight of the composition. Alternatively, the hydrocolloid may be in the form of a powder whose average particle size is less than 100 μm, and preferably less than 50 μm.

The swelling agent should be non-volatile, and allow the gel to remain as a gel during use, hence preserving the swollen condition of the hydrocolloid. Varieties of non-volatile swelling agents include room temperature liquid polyols (including polyhydric alcohols) such as glycerol; room temperature solid polyols (including polyhydric alcohols) such as sorbitol, erythritol, threitol, ribotol, arabinitol, xylitol, allitol, talitol, mannitol, glucitol, glactitol, iditol, pentaerythritol, heptitol, octitol, nonitol, decitol, and dodecitol, blended with a room temperature liquid polyol; monoanhydroalditols (such as styracitol, polyalitol, D-fructose, 1,4 anhydro-D-mannitol and 1,4 anhydro-D-glucitol) blended with a room temperature liquid polyol; monosaccharides (such as pentoses, hexoses, and heptoses) blended with a room temperature liquid polyol; and ether alcohols blended with a room temperature liquid polyol.

Hydrocolloid dressings often comprise a wafer constructed from a thin layer of polyurethane film with an adhesive contact layer containing a hydrocolloid composition and securing the dressing to the mucosal membrane, and the polyurethane film being impermeable to water and microorganisms. Hydrocolloid dressings may be prepared by dispersing a composition in gel form of hydrocolloids with a swelling agent into a strong pressure sensitive adhesive. Alternatively, the gel and the adhesive may be mixed in a latex solution. Alternatively, exemplary products are available commercially, for example DuoDERM™ (ConvaTec Canada, 555, Dr. Frederik Philips, Suite 110, St-Laurent, Quebec, H4M 2×4); and Tegasorb™ (3M Health Care, 300 Tartan Drive, London, Ontario, Canada, N5V 4M9). The hydrocolloid dressing may be impregnated with a solution or powder of the antimicrobial metals by blending the solution or powder of the antimicrobial metal into a liquid phase during the manufacture of the hydrocolloid dressing, or by sprinkling and then pressing a powder of the antimicrobial metal into the surface of the hydrocolloid dressing. Further, the hydrocolloid dressing can be used with a topical formulation of the antimicrobial metals of this invention. Upon application, the dressing surface gels upon continued contact with moisture, secretions or exudate from the mucosal membrane. With the incorporation of an antimicrobial metal such as silver (0.01–10%, preferably 0.1–1% by weight), the dressing is advantageous in being impermeable to water and microorganisms, and presenting antimicrobial and anti-inflammatory effects as mediated by the antimicrobial metal.

4. Gels—Nanocrystalline gels may be formed from the nanocrystalline metal powder in admixture with gelling agents such as hydrocolloids and hydrogels in powder form. Exemplary gelling agents include carboxymethyl cellulose (CMC), polyvinyl alcohol (PVA), collagen, pectin, gelatin, agarose, chitin, chitosan, and alginate, with the gelling agent comprising between about 0.01–20% w/v.
5. Creams, Lotions, Pastes, Ointments, Foams—The antimicrobial metals may be incorporated into creams, lotions, pastes, ointments or foams formulated with nanocrystalline powders or solutions of the antimicrobial metals, for example as emulsions or with drying emollients. Ointments and creams can be formulated with an aqueous or oily base with the addition of suitable thickening and/or gelling agents. Such bases may include water and/or an oil such as liquid paraffin or a vegetable oil such as peanut oil or castor oil. An exemplary base is water. Thickening agents which can be used according to the nature of the base include aluminum stearate, hydrogenated lanolin, and the like. Further, lotions can be formulated with an aqueous base and will, in general, also include one or more of the following: stabilizing agents, emulsifying agents, dispersing agents, suspending agents, thickening agents, colouring agents, perfumes, and the like. Ointments and creams can also contain excipients, such as starch, tragacanth, cellulose derivatives, polyethylene glycols, silicones, bentonites, silicic acid, and talc, or mixtures thereof. Lotions may be formulated with an aqueous or oily base and will, in general, also include one or more of the following: stabilizing agents, emulsifying agents, dispersing agents, suspending agents, thickening agents, colouring agents, perfumes, and the like. Foams may be formed with known foaming or surface active agents.
6. Liquids—The crystalline forms of the antimicrobial metals may be incorporated into liquids, formulated as solutions, dispersions or suspensions by dissolving nanocrystalline coatings or powders of the antimicrobial metals, for example as topical solutions, aerosols, mists, sprays, drops, and instillation solutions for body cavities and tubes such as the bladder, prostate, perintheal, pericharcliar, pleural, intestinal and ailimentary canal. Administration of the antimicrobial metal to the mucosal membrane may be performed by aerosol, which can be generated by a nebulizer, or by instillation.

The antimicrobial or noble metal may be administered alone, or with a carrier such as saline solution, DMSO, an alcohol or water. An effective daily amount of the antimicrobial or noble metal will vary with the subject, but will be less than is toxic while still providing a therapeutic effect.

Solutions and formulations of the antimicrobial metals may lose some activity with aging and are thus either stabilized or generated fresh for administration. Alternatively, the antimicrobial metals may be packaged for convenient solution generation, for instance as tea bag-type infusers. Other two part or two phase systems may be used in which the nanocrystalline metal is separated from the water or alcohol-based electrolyte, for example in a multicomponent kit form, as set out herein.

Concentrations of the antimicrobial metal species in solution will vary according to the application, formulation and subject, but will generally range from 1–5000 μg/ml, more preferably 20–3000 μg/ml, more preferably 40–800 μg/ml, and most preferably 50–500 μg/ml. Methods of generating liquids with appropriate concentrations of the antimicrobial metal through pH control are set out below and in the examples. Control over droplet size for aerosol formulations is also addressed below.

7. Transdermal Patch—Transdermal patches may provide controlled delivery of the antimicrobial metal to the mucosal membrane. For example, an adhesive patch or adhesive matrix patch, can be prepared from a backing material and an adhesive, such as an acrylate adhesive. Powders or solutions of the antimicrobial metal may be formulated into the adhesive casting solution and allowed to mix thoroughly. The solution is cast directly onto the backing material and the casting solvent is evaporated in an oven, leaving an adhesive film. Alternatively, a polyurethane matrix patch can be employed to deliver the antimicrobial metal to the mucosal membrane. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and drug to the prepolymer results in the formation of a tacky firm elastomer that can be directly cast onto the backing material.

C. Sterilization

Dressings, coatings, powders or formulations of the nanocrystalline antimicrobial metal formed with atomic disorder are preferably sterilized without applying excessive thermal energy, which can anneal out the atomic disorder, thereby reducing or eliminating a useful release of antimicrobial metal species. Gamma radiation is preferred for sterilizing such dressings, as discussed in WO 95/13704. Electron beam and ethylene oxide sterilization techniques can also be used.

It should be appreciated with respect to dressings, that the use of ultrasonic welding to laminate the layers of dressings with nanocrystalline coatings formed from antimicrobial metals with atomic disorder is advantageous since it achieves bonding in localized spots and avoids applying heat to any significant portion of the dressing, thereby avoiding any significant reduction in the solubility of the antimicrobial metals through annealing out of the atomic disorder.

The sterilized dressings, coatings, powders or formulations should be sealed in packaging, containers or kits which limits moisture and light penetration to avoid additional oxidation or reduction of the antimicrobial metal. Polyester peelable pouches are exemplary. The shelf life of coatings or powders thus sealed is over one year.

D. Formulating Dosages and Treatment

Typically, the nanocrystalline antimicrobial metals will be formulated from the active ingredient, namely nanocrystalline powders or coatings of the antimicrobial metals, or dissolved species from such powders or coatings, in the one or more of the formats set out above. Dressings or powders of the nanocrystalline antimicrobial metals may be applied directly to the mucosal membrane, or they may be formulated as set out below. Depending on the particular application and dosage form, the powder size might be controlled to less than 2 μm, more preferably to less than 1 μm.

In the pharmaceutical compositions, the amount of the nanocrystalline metal powder may range broadly from about 0.001% to about 30% by weight, but will more preferably fall in the range of from about 0.01 to 10% by weight, and most preferably in the range of about 0.1 to 5% by weight. Typical coating thicknesses are in the range of 150 to 3000 nm thick. Thicker coatings, up to 10,000 nm thick, can be used to generate powders of the antimicrobial metal. Coatings of the nanocrystalline antimicrobial metals may be very thin, or thick, depending on the desired duration of application on the patient. As liquid formulations, the amount of dissolved antimicrobial metal will typically range between about 0.001 to 10% by weight, more preferably 0.01 to 1% by weight.

Besides the active ingredient, pharmaceutical compositions may also include non-toxic, pharmaceutically acceptable carriers, diluents and excipients, suitable for topical application, as are well known, see for example Merck Index, Merck & Co., Rahway, N.J.; and Gilman et al., (eds) (1996) Goodman and Gilman's: The Pharmacological Bases of Therapeutics, $8^{th}$ Ed., Pergamon Press. For standard dosages of conventional pharmacological agents, see, e.g., Physicians Desk Reference (1997 Edition); and U.S. Pharmacopeia National Formulary (1995), United States Pharmacopeial Convention Inc., Rockville, Md.

Dosage forms for the topical administration of compositions of the nanocrystalline antimicrobial metals include various mixtures and combinations that can be applied topically and will permit even spreading and absorption into the cutaneous surfaces. Examples include sprays, mists, aerosols, lotions, creams, solutions, gels, ointments, pastes, emulsions, foams and suspensions. The active compound can be mixed under sterile conditions with a pharmaceutically acceptable carrier, and with any preservatives, buffers, or propellants which may be required. Topical preparations can be prepared by combining the antimicrobial metal powder with conventional pharmaceutically acceptable carriers commonly used in topical dry, liquid, cream and aerosol formulations. Ointment and creams can, for example, be formulated with an aqueous or oily base with the addition of suitable thickening and/or gelling agents. An exemplary base is water. Thickening agents can be used according to the nature of the base. Lotions can be formulated with an aqueous base and will, in general, also include one or more of the following: stabilizing agents, emulsifying agents, dispersing agents, suspending agents, thickening agents, coloring agents, perfumes, and the like. Powders can be formed with the aid of any suitable powder base, e.g., talc, lactose starch and the like. Drops can be formulated with an aqueous base or non-aqueous base, and can also include one or more dispersing agents, suspending agents, solubilizing agents, surface active agents and the like.

Ointments, pastes, creams and gels also can contain excipients, such as starch, tragacanth, cellulose derivatives, silicones, bentonites, silicic acid, and talc, or mixtures thereof. Powders and sprays also can contain excipients such as lactose, talc, silicic acid, aluminum hydroxide, and calcium silicates, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, for instance inert gases such as nitrogen, carbon dioxide, argon or neon.

Multiple inactive ingredients are generally incorporated in topical formulations to improve cosmetic acceptability, and are optional ingredients in the formulations. Such ingredients are included only in therapeutically acceptable forms and amounts. Examples of ingredients are emulsifiers, emollients, thickening agents, solvents, hydrating or swelling agents, flavours, sweetening agents, surface active agents, colouring agents, anti-foaming agents, preservatives, fragrances, and fillers may also be added, as is well known in the art; for example, preservatives such as methyl paraben and propyl paraben, texturizing agents, thickeners, anticoagulants such as heparin, β-glucan, hormones, hyaluronic acid, immune potentiating agents such as adjuvants and cytokines such as epidermal growth factor, platelet derived growth factor, transforming growth factor and interleukins, and bone morphogenetic proteins, and the like. Polyvinyl alcohol is a particularly preferred gelling polymer and also acts as a texturizing agent, methyl or propyl parabens are particularly preferred preservatives. These other agents may be included in amounts in the range of 0.1 to 5 wt %.

Surface active agents or foaming agents may be added to the formulations and are particularly advantageous for addition to liquid formulations for aerosol or foam applications, to form foams for applications such as to treat STD's or aerosols for application for respiratory disorders. Surface active agents are also useful for such coated substrates as dental floss. Exemplary surface active agents are listed in for instance WO 02/02128 to The Proctor & Gamble Company, published Jan. 10, 2002, and in U.S. Pat. No. 5,875,799 to Petrus, issued Mar. 2, 1999. Particularly useful are sodium lauryl sulfate, sodium lauroyl sarconsinate, sodium alkyl sulfate, and phospholipids such as lecithin and sphingomyelin.

All agents must be non-toxic and physiologically acceptable for the intended purpose, and must not substantially interfere with the activity of the nanocrystalline antimicrobial metals so as to deleteriously affect the antimicrobial effect or the anti-inflammatory activity. Ingredients are thus only included in therapeutically acceptable amounts. Ingredients to be generally avoided or limited in the formulations of the present invention, at least in amounts greater than 0.01 wt %, are glycerin, glycerols, chloride salts, aldehydes, ketones, long chain alcohols, and triethanolamine.

The dosage of the active ingredients depends upon many factors that are well known to those skilled in the art, for example, the particular form of the active ingredient, the condition being treated, the age, weight, and clinical condition of the recipient patient, and the experience and judgement of the clinician or practitioner administering the therapy. A therapeutically effective amount of the nanocrystalline antimicrobial metal provides either subjective relief of symptoms or an objectively identifiable improvement as noted by the clinician or other qualified observer. The dosing range varies with the metal used, its form, the route of administration and the potency of the particular compound.

When the formulation is in the form of a dressing, the dressing is placed on the affected portion of the mucosal membrane and, depending on the degree of moisture at the membrane, may be further moistened with drops of sterile water or, for example 70% ethanol, in order to activate the coating for release of antimicrobial or noble metal species. The dressing may be then secured in place with an occlusive or semi-occlusive layer, such as an adhesive tape or polyurethane film, which keeps the dressing in a moist environment. In use, the dressings are kept moist, at 100% relative humidity. Adding sterile water initially to activate the antimicrobial or noble metal coating is needed, and then as needed to maintain the dressing in a moist condition. Dressings may be changed as required for observation and cleaning. Preferably dressings are changed daily, but could be left longer, such as 3 days, and can provide a therapeutic effect for a much longer period of time.

Other forms of formulations, such as occlusions, gels, pastes, ointments, creams, emulsions, foams, and liquids may be prepared in stable forms, or more preferably are prepared fresh from one or more phases, for instance in multi component kit form, so as to avoid aging and to maximize the therapeutic effectiveness of the antimicrobial metal component. Formulations are best used within about 30 days after combining the phases. Suitable kits or containers are well known for maintaining the phases of formulations separate until the time of use. For instance, the antimicrobial metal in powder or coated substrate form may be packages separately from therapeutically acceptable carriers, and possibly other ingredients for mixing at the time of use. The separate coated substrate may be in dressing or patch form for direct application, or may take other suitable forms to generate liquid formulations and the like, such as a coating on the inside surface of a vial or container, a liner, a porous shaped mesh, a filtering surface, a mesh, or a film. For example, the antimicrobial metal may be provided in a "tea bag"-type infuser or pouch, for generating liquid formulations at the time of use. The tea bag-type infuser is advantageous in that the pouch may serve as a filter for small particulates of the powder that may be detrimental to administration for some applications such as aerosols for respiratory disorders. A kit containing the dressing, coated substrate or powder may provide a sterile carrier such as water (and other ingredients) in a separate container in dosage specific amounts. As used herein, the term "kit" is meant to refer to packaged formulations, whether the ingredients are in separate phases or mixed, and thus for example, may include a gel in a tube with all ingredients in admixture, or any formulation wherein the ingredients are separated from each other.

Formulations for respiratory disorders may be delivered as dry powders in dry powder inhalers, or they may be formulated in liquid formulations for delivery in metered dose inhalers, aerosols, mists or sprays.

For liquid formulations, in order to increase the amount of antimicrobial or noble metal solubilized in the solution, the pH of the solution during dissolution may be lowered to less than pH 6.5, more preferably to the range of 3.5 to 6.5, with such acidifying agents as carbon dioxide (which generated carbonic acid in solution). This pH range will typically generate concentrations of silver from atomic disordered silver from 85 μg/ml to 370 μg/ml, and can be adjusted for different desired concentrations. Dissolution of the antimicrobial metal will typically raise the pH to 6.5 to 7.0.

Administration as aerosols produces droplets preferably less than 10 μm in size, more preferably less than 5 μm in size, most preferably 1–3 μm in size. Control of the droplet size is important both to control the dosage delivered and to enhance delivery to the target tissues, e.g., where the aerosol is inhaled through the mouth, large droplets of about 10 μm tend to stay in the throat whereas small droplets (e.g., approximately 1–3 μm) tend to travel to the alveolar region of the lungs. Thus, depending on the dosage required and the target tissue, it may be important to regulate the droplet size of the aerosol. In this respect, it has been found that droplet size can be regulated, to at least some extent, by the mechanical mister which is used to produce the aerosol. In addition, the aerosol's droplet size can be adjusted, to at least some extent, by modifying the surface tension of the solution. More particularly, the solution of the antimicrobial metal typically has water as its solvent, and water has a relatively high surface tension, so it is relatively straightforward to create an aerosol having relatively small droplet size. Surface active agents can be added to the solution so as to reduce the surface tension of the solution, to create an aerosol having a relatively large droplet size. By way of example, such surface active agents may comprise sodium alkyl sulfates, sodium lauryl sulfate, sodium lauroyl sarconsinate, phospholipids, e.g., lecithin, sphingomyelin, etc.

Depending on the application, solutions generated from powders of the antimicrobial metal should avoid inclusion of particulates larger than 2 μm, and more preferably no larger than 1 μm (i.e., submicron) to avoid deliterious immune responses or toxic effects. Larger particulates may be removed by, for example filtration. Particulates may be formed in the liquid and can be removed, for example by filtration. For instance, silver carbonates may be formed on reaction with the carbonic acid used to acidify the solution. Particulate generation may also be limited by diluting the carbonic acid in solution.

The aerosol may be created by passing a liquid solution of the antimicrobial metal through a mechanical mister (e.g., a nebulizer) and may be applied directly with a pressurized pack (e.g., via a hand inhaler with a propellant such as carbon dioxide or other gas, with a valve metered dosage) or through some other delivery system (e.g., an oxygen tent, etc.).

The invention provides methods of treating, by administering a therapeutically effective amount of a nanocrystalline antimicrobial or noble metal powder, or a solution derived from a nanocrystalline antimicrobial or noble metal, as either a topical formulation, or as a coating on medical dressing, applied to the locally affected area of the mucosal membrane. A therapeutically effective amount may be determined by testing formulations containing the nanocrystalline antimicrobial or noble metals by in vitro or in vivo testing. Formulations may be applied one or more times a day. Dressings coated with the nanocrystalline antimicrobial or noble metals may be changed daily, or even less frequently, and should be kept in a moist condition with the addition of saline, alcohols, or more preferably sterile water, in order to release ions, atoms, molecules or clusters of the nanocrystalline metal, on a sustained basis.

E. EXAMPLES

Example 1

Preparation of Nanocrystalline Silver Coatings on Dressings

This example shows the preparation of a bilayer nanocrystalline silver coating on a dressing material. A high density polyethylene dressing, DELNET™ or CONFORMANT 2™ was coated with a silver base layer and a silver/oxide top layer to generate a coloured antimicrobial coating having indicator value. The coating layers were formed by magnetron sputtering under the conditions set out in Table 1.

TABLE 1

Sputtering conditions

| Sputtering Conditions: | Base Layer | Top Layer |
|---|---|---|
| Target | 99.99% Ag | 99.99% Ag |
| Target Size | 20.3 cm diameter | 20.3 cm diameter |
| Working Gas | 96/4 wt % $Ar/O_2$ | 96/4 wt % $Ar/O_2$ |
| Working Gas Pressure | 5.33 Pa (40 mT) | 5.33 Pa (40 mT) |
| Power | 0.3 kW | 0.15 kW |
| Substrate Temperature | 20° C. | 20° C. |
| Base Pressure | $3.0 \times 10^{-6}$ Torr ($4 \times 10^{-4}$ Pa) | $3.0 \times 10^{-6}$ Torr ($4 \times 10^{-4}$ Pa) |
| Anode/Cathode Distance | 100 mm | 100 mm |
| Sputtering Time | 7.5–9 min | 1.5 min |
| Voltage | 369–373 V | 346 V |

The resulting coating was blue in appearance. A fingertip touch was sufficient to cause a colour change to yellow. The base layer was about 900 nm thick, while the top layer was 100 nm thick.

To establish that silver species were released from the coated dressings, a zone of inhibition test was conducted. Mueller Hinton agar was dispensed into Petri dishes. The agar plates were allowed to surface dry prior to being inoculated with a lawn of *Staphylococcus aureus* ATCC No. 25923. The inoculant was prepared from Bactrol Discs (Difco, M.), which were reconstituted as per the manufacturer's directions. Immediately after inoculation, the coated materials to be tested were placed on the surface of the agar. The dishes were incubated for 24 hr. at 37° C. After this incubation period, the zone of inhibition was calculated (corrected zone of inhibition=zone of inhibition−diameter of the test material in contact with the agar). The results showed a corrected ZOI of about 10 mm, demonstrating good release of silver species.

The coating was analyzed by nitric acid digestion and atomic absorption analysis to contain 0.24+/−0.04 mg silver per mg high density polyethylene. The coating was a binary alloy of silver (>97%) and oxygen with negligible contaminants, based on secondary ion mass spectroscopy. The coating, as viewed by SEM, was highly porous and consisted of equiaxed nanocrystals organized into coarse columnar structures with an average grain size of 10 nm. Silver release studies in water demonstrated that silver was released continuously from the coating until an equilibrium concentration of about 66 mg/L was reached (determined by atomic absorption), a level that is 50 to 100 times higher than is expected from bulk silver metal (solubility<1 mg/L).

By varying the coating conditions for the top layer to lengthen the sputtering time to 2 min, 15 sec., a yellow coating was produced. The top layer had a thickness of about 140 nm and went through a colour change to purple with a fingertip touch. Similarly, a purple coating was produced by shortening the sputtering time to 1 min, to achieve a top layer thickness of about 65 nm. A fingertip touch caused a colour change to yellow.

To form a three layer dressing, two layers of this coated dressing material were placed above and below an absorbent core material formed from needle punched rayon/polyester (SONTARA™ 8411). With the silver coating on both the first and third layers, the dressing may be used with either the blue coating side or the silver side in the mucosal membrane facing position. For indicator value, it might be preferable to have the blue coating visible. The three layers were laminated together by ultasonic welding to produce welds between all three layers spaced at about 2.5 cm intervals across the dressing. This allowed the dressing to be cut down to about 2.5 cm size portions for smaller dressing needs while still providing at least one weld in the dressing portion.

The coated dressings were sterilized using gamma radiation and a sterilization dose of 25 kGy. The finished dressing was packaged individually in sealed polyester peelable pouches, and has shown a shelf life greater than 1 year in this form. The coated dressings can be cut in ready to use sizes, such as 5.1×10.2 cm strips, before packaging. Alternatively, the dressings may be packaged with instructions for the patient or clinician to cut the dressing to size.

Additional silver coated dressings were prepared in a full scale roll coater under conditions to provide coatings having the same properties set out above, as follows:

a) the dressing material included a first layer of silver coated DELNET, as set out above, laminated to STRATEX, AET, 8.0NP$_2$-A/QW, which is a layer of 100% rayon on a polyurethane film.

b) Silver Foam Dressing—three layers of silver coated high density polyethylene prepared as above, alternating with two layers of polyurethane foam, L-00562-6 Medical Foam, available from Rynel Ltd., Bootbay, Me., USA.

The HDPE mesh coated with silver can be used to generate solutions containing silver species for liquid formulations and the like, as set forth in examples below (AgHDPE). Similar coating conditions are used on substrates such as alginate and CMC as set out in later examples.

Example 2

Preparation of Atomic Disordered Nanocrystalline Silver Powders

Nanocrystalline silver coatings were prepared by sputtering silver in an oxygen-containing atmosphere directly onto an endless stainless steel belt of a magnetron sputtering roll coater, or onto silicon wafers on the belt. The belt did not need to be cooled. The coatings were scraped off with the belt with suspended metal scrapers as the belt rounded the end rollers. For the coated silicon wafers, the coatings were scraped off with a knife edge. The sputtering conditions were as follows:

TABLE 2

| Sputtering Conditions | |
|---|---|
| Target: | 99.99% Ag |
| Target Size (individual, 23 targets): | 15.24 cm × 1216.125 cm |
| Working Gas: | 75:25 wt % $Ar/O_2$ |
| Working Gas Pressure: | 5.33 Pa (40 mTorr) |
| Total Current: | 40 A |
| Base Pressure: | $5.0 \times 10^{-5}$ Torr (range: $1 \times 10^{-4}$–$9 \times 10^{-7}$ Torr; $1 \times 10^{-2}$–$1.2 \times 10^{-4}$ Pa) |
| Sandvik Belt Speed: | 340 mm/min |
| Voltage: | 370 V |

Note
pressure conversions to Pa herein may not be accurate, most accurate numbers are in Torr, mTorr units.

The powder had a particle size ranging from 2 μm to 100 μm, with grain or crystallite size of 8 to 10 nm (i.e., nanocrystalline), and demonstrated a positive rest potential.

Similar atomic disordered nanocrystalline silver powders were formed as set forth hereinabove by magnetron sputtering onto cooled steel collectors, under conditions taught in the prior Burrell et al. patents to produce atomic disorder.

Example 3

Silver solutions were prepared by immersing AgHDPE mesh from dressings prepared as in Example 1 in reverse osmosis water that had been pretreated with $CO_2$ in order to reduce the pH. Two different concentrations of silver solutions were prepared by this method, the concentrations being 85 μg/ml, and 318 μg/ml. Solutions of silver nitrate were also prepared to use as comparisons in the experiments. The concentrations of the silver nitrate were 103 ppm of silver and 295 ppm of silver as determined by Atomic Absorption Spectroscopy.

The solutions were in turn placed in an ultrasonic nebulizer that created small droplets containing dissolved and suspended parts of the silver solution. The output from the nebulizer was directed into a chamber made from a stainless steel frame and base. Petri dishes containing Mueller Hinton agar streaked with 4 h old cultures of *Pseudomonas aeruginosa* and *Staphylococcus aureus,* were exposed to the silver solution aerosols and the silver nitrate aerosols.

The results of the tests show that silver aerosols of this invention transmit the antimicrobial activity of the dressings to remote sites, and such aerosols are more effective than comparable concentrations of silver nitrate.

In many instances the delivery of antimicrobial materials may most expeditiously be accomplished by using aerosols (e.g. treatment of pneumonia). The drawback of aerosols is the requirement for a high concentration of the active ingredient to ensure that a sufficient amount is delivered to achieve the biological effect desired without causing problems with the carrier solvent (e.g. water). It is preferably that the equipment for producing an aerosol that contains the dissolved and suspended components of nanocrystalline silver form droplets of aerosol direct from the liquid form, and the aerosol droplets must be small enough to reach the lungs. This means the droplets should be less than approximately 10 μm. To meet these requirements the aerosol is not created by first evaporating the liquid then condensing it to form droplets. Rather, aerosols are generated by 1) mechanical disruption of the liquid, or 2) air under pressure passing through some form of orifice that combines the air and the liquid in a way that creates droplets instead of evaporating the liquid.

Several experiments were carried out with silver solutions of this invention and silver nitrate solutions to determine if the antimicrobial activity of the dressing could be transferred through a direct droplet aerosol to a Petri dish.

a) Methods i) Equipment

The method used for the current tests was the mechanical method in the form of an ultrasonic nebulizer. For convenience an ultrasonic humidifier was used. The liquid containing the dissolved and suspended silver from the dressing of Example 1 was placed in the water reservoir of the humidifier. When power was applied to the humidifier aerosol droplets of dissolved and suspended silver were generated and flowed from the output nozzle.

A test chamber was constructed using a stainless steel frame with a transparent plastic covering. The frame was placed on a stainless steel base plate. The output nozzle from the humidifier was modified so that the aerosol could be directed into the chamber at a height of approximately 30 cm from the base. The plates and other test samples were placed on the stainless steel plate and exposed to the aerosol for a prescribed length of time.

ii) Solutions

Solution 1—A silver containing solution was prepared by immersing 518 sq. inches of the dressing from Example 1 in 1 L of reverse osmosis water, which was treated with $CO_2$ to maintain a pH of 6.5. After 20 minutes the concentration of silver in the water was 85 μg/ml.

Solution 2—A solution containing 370 μg/ml of silver from a dressing from Example 1 was prepared as follows: 1 L of reverse osmosis water was purged with commercial grade carbon dioxide until the pH was 4.3.

Sufficient dressing was added to bring the pH up to 6.5. At that time, the silver concentration was 370 μg/ml.

Solution 3—Ag as $AgNO_3$ was prepared by dissolving 0.157 g of $AgNO_3$ into 1 L of reverse osmosis water and mixed until dissolved. The solution was analyzed by Atomic Absorption Spectroscopy and found to be 102.9 ppm of silver.

Solution 4—Ag as $AgNO_3$ was prepared by dissolving 0.427 g of $AgNO_3$ into 1 L of reverse osmosis water and mixed until dissolved. The solution was analyzed by Atomic Absorption Spectroscopy and found to be 295 ppm of silver.

iii) Aerosolization

Petri dishes, containing Mueller Hinton agar, were streaked with 4 h old cultures of *Pseudomonas aeruginosa* or *Staphylococcus aureus*. The plates were then weighed and their exposed outer surfaces were coated with Parafilm to prevent condensation from occurring on these surfaces. These plates were placed in the aerosol chamber uncovered. The ultrasonic nebulizer was then started and run for 53 minutes. The plates were then removed from the chamber, the plastic was removed and the dishes re-weighed so that the amount of moisture loss/gain could be determined.

The plates were then placed in a 35° C. incubator for 16 h. After incubation the pattern and amount of growth was assessed on the plates for both organisms.

iv) Viability Assessment

Three of the six plates made for each organism were tested to determine if the antimicrobial effect was cidal or static in nature. This was accomplished by rinsing or placing a piece of the clear section of agar in the Petri dish plates into Tryptic soy broth in a test tube and incubating for 4 h or 16 h. If the medium turned turbid in 4 h it would indicate that the antimicrobial affect was bacteriostatic in nature. If the organisms took more than 16 h to grow, as indicated by turbidity, it was considered an indication that both static and cidal effects occurred. If no growth occurred the effect was bactericidal.

v) Results—Solutions 1 and 2 Results are Summarized Below.

TABLE 3

Solutions 1 and 3 Results

| | Silver from Dressing | | $AgNO_3$ | |
|---|---|---|---|---|
| Organism | *P. aeruginosa* | *S. aureus* | *P. aeruginosa* | *S. aureus* |
| Ag concentration (μg/ml) | 85 | 85 | 99 | 99 |
| pH of test solution | 6.5 | 6.5 | ≈6.5 | ≈6.5 |
| Exposure time (minutes) | 53 | 53 | 53 | 53 |
| Exposed area (sq. in) | 9.8 | 9.8 | 9.8 | 9.8 |
| Weight gain (g) | 0.8 | 0.8 | 1.05 | 1.05 |
| Growth at 16 h | 0 | 0 | 0 | ++++ |
| (0–++++) at 48 h | 0 | ++ | 0 | ++++ |
| Viable 4 h | No | Yes | No | Yes |
| 16 h | Yes | Yes | Yes | Yes |

TABLE 4

Solutions 2 and 4 Results

| | Silver from Dressing | | $AgNO_3$ | |
|---|---|---|---|---|
| Organism | *P. aeruginosa* | *S. aureus* | *P. aeruginosa* | *S. aureus* |
| Ag concentration (μg/ml) | 370 | 370 | 300 | 300 |
| pH of test solution | 6.5 | 6.5 | ≈6.3 | ≈6.3 |
| Exposure time (minutes) | 53 | 53 | 53 | 53 |
| Exposed area (sq. in) | 9.8 | 9.8 | 9.8 | 9.8 |

TABLE 4-continued

| Solutions 2 and 4 Results | | | | |
|---|---|---|---|---|
| | Silver from Dressing | | $AgNO_3$ | |
| Organism | *P. aeruginosa* | *S. aureus* | *P. aeruginosa* | *S. aureus* |
| Weight gain (g) | 1.14 | 1.14 | 1.12 | 1.12 |
| Growth at 16 h | 0 | 0 | 0 | 0 |
| (0–++++) at 48 h | 0 | 0 | 0 | +++ |
| Viable 4 h | No | No | No | No |
| 16 h | No | No | No | N/A |

vi) Discussion

At the low concentration of silver in solution, the dressing generated silver was effective in controlling the growth of both organisms while the silver nitrate only prevented the growth of *P. aeruginosa.* Viability tests showed that at the low concentration, neither form of silver was completely bacteriocidal although the poor growth on the dressing aerosol treated plates compared to the silver nitrate treated plates suggests that a significant log reduction occurred in the dressing aerosol treated plates.

At a higher concentration of silver, both dressing generated silver (370 μg/ml) and $AgNO_3$ (300 μg/ml) were effective at controlling *P. aeruginosa.* Since no re-growth occurred, it is assumed that the agent at this concentration were bactericidal. Silver generated from the dressing was more effective than $AgNO_3$ at controlling *S. aureus.* No re-growth occurred on any plates or in the broth indicating a total kill of the organism while in the $AgNO_3$ treatment, a large number of organisms grew at 16 h.

Based on weight gain during aerosol treatments a dose per unit area can be calculated. In each case for solution 1 the dose was 8.5 μg/sq. inch while for solution 2 the dose was 38 μg/sq. inch. These doses, on a per lung basis, would be less than 10 mg of silver per hour of treatment. Each hour of treatment with dressing generated silver aerosols appears to provide at least 48 h of protection. Therefore the dose per day, from the high concentration treatment, would be about 5 mg or a little less than the silver released by 2 sq. inches of SSD per day.

A most significant advantage of using dressing generated silver may be the lack of a toxic cation such as $NO_3$ or sulfadiazine.

Overall, the example demonstrated that the dressing generated aerosols are operative to transmit the antimicrobial activity of the dressings to remote sites. Furthermore, the dressing generated aerosols were more effective than comparable concentrations of silver nitrate.

Example 4

Aerosolized Silver Solutions in Rats a) Materials And Methods i) Solutions From Atomically Disordered Silver Dressings A solution was prepared by sparging $CO_2$ through 400 ml of reverse osmosis water for 30 minutes at a flow rate of 1 L/min. The beaker of water was covered with a piece of parafilm to assist in maintaining a saturated $CO_2$ environment. This process resulted in the pH of the water dropping to about 4. At this point, approximately 600 square inches of silver-coated net (AgHDPE) prepared as in Example 1 was added to the water and stirred for approximately 40 minutes resulting in an elevation of the pH to approximately 6.5. The solution was then transferred to a medical nebulizer and connected to an oxygen cylinder with a flow rate of 10 L/min. The outflow of the nebulizer was connected to a sealed animal chamber housing the rats to be dosed. Only the "test" rats (15 randomly assigned animals) received the dosing. The rats received two, one-hour aerosol administrations of the solution on the day of infection. Thereafter, the test rats were dosed three times per day for an additional three days.

ii) Animals

Thirty male Sprague-Dawley rats were obtained from the University of Calgary, Alberta, Canada breeding colony. These animals were specific-pathogen free and weighed approximately 300 g. The animals were housed in groups of 5 in plastic cages with wire mesh tops. The rats had access to fresh water and rat chow ad libitum. All animals were maintained in an appropriate facility with 12-hour light/dark cycles and constant temperature and humidity, according to facility standard operating procedures. The protocol was approved by the University of Calgary Animal Care Committee and was conducted in accordance with guidelines established by the Canadian Council on Animal Care.

iii) Bacteria

The bacteria used for infection of these animals were *Pseudomonas aeruginosa* strain 579. The dose was previously titrated to ascertain that a dose of up to $10^{10}$ CFU was not lethal for the animals. The bacteria were grown overnight in Tryptic soy broth, washed once in sterile PBS, and re-suspended in a 1/10 volume of sterile PBS.

iv) Infection

The rats were anesthetized by inhalation of 2% halothane. A 50 μL volume of bacterial suspension was intratracheally administered into the bronchi of each rat. This was performed non-surgically on intubated animals. The infection process resulted in the instillation of approximately $2\times10^9$ CFU into the lungs of each animal.

iv) Sampling

On each day, a number of animals were sacrificed. The lungs of the animals were aseptically removed, homogenized, and plated to determine bacterial levels. A few animals were also subjected to bronchoalveolar lavage prior to removal of the lungs. In several cases, lung homogenates and/or lavage fluids were reserved for silver analysis.

After the first batch of the silver solution was prepared, total silver analysis indicated that there was about 255 ppm of total silver in solution. The solution was reserved for several hours until after the next dosing of the animals. A second silver analysis indicated that the total silver in solution had dropped to about 166 ppm. The reason for the drop was immediately apparent as the silver had visibly precipitated out of solution and had deposited on the surface of the nebulizer. One other batch of freshly prepared solution had a total silver concentration of 337 ppm. Regardless of the actual numbers, the process of generating the silver solution results in a significant quantity of silver in the solution that is aerosolized into the dosing chamber.

The dosing chamber is not perfect. Although significant amounts of mist are generated into the chamber, the rats tend to lie on top of one another and are probably exposed to vastly different levels of the silver mist.

b) Results i) Pulmonary Bacterial Levels

| Day | Log CFU/Test Lung | Log CFU/Control Lung |
|---|---|---|
| 1 | 6.2 | 7.3 |
| 2 | 4.1 | 7.8 |
| 3 | 0 | 6.2 |
| 4 | 3.5 | 4.8 |

The bacteriological results gathered from the lungs of the treated and control animals demonstrated a sharper decline in the numbers of bacteria present in the lungs following treatment with the silver mist as compared to controls. The results indicate that, in spite of the small sample sizes and inconsistent exposures, a difference could still be noted. There was considerable variation in the numbers of bacteria recovered from individual animals within each treatment group and, therefore, there was no significant difference in the results. Gross examination of excised lungs suggested that there may have been less apparent damage to the lungs in the animals treated with the silver mist as compared to the untreated, infected animal. This was very encouraging given the potential anti-inflammatory effects of the nanocrystalline silver technology.

ii) Pulmonary Silver Levels

| Sacrifice Date | Rat Description | Total Silver Level | Average |
|---|---|---|---|
| 36999 | Silver mist 1 | 0.50 ppm | |
| 36999 | Silver mist 2 | 1.13 ppm | 0.74 ppm |
| 36999 | Silver mist 3 | 0.58 ppm | |
| 37000 | Silver mist 4 | 0.73 ppm | |
| 37000 | Silver mist 5 | 0.70 ppm | 0.72 ppm |
| 37000 | Control 1 | 0.08 ppm | |
| 37000 | Control 2 | 0.10 ppm | 0.09 ppm |

The results of the silver analysis appear to indicate that the amount of silver in the lung either plateaus or each dose of silver mist deposits a certain amount of silver within the lung and this level is significantly diminished prior to the next dosing of the animals.

The results of this experiment indicated that the method employed to prepare the silver mist solution was reasonably reproducible and yielded relatively high concentrations of silver in solution. However, the silver was prone to precipitation and should be freshly prepared prior to each dosing period. A lengthy period between preparation and dosing, although resulting in a decrease in the amount of silver in solution, did not result in a complete elimination of the silver from the solution or even result in the silver concentration dropping to very low levels.

The method employed for exposing the rats to the mist is also prone to significant variation due to the piling up of the rats and the resultant inconsistent exposure to the silver-containing mist. However, the silver analyses suggested that a reasonably uniform dose of silver was achieved when only a few animals were present within the dosing chamber.

Regardless of the difficulties associated with the experiment, the results were indicative of a therapeutic modality for pulmonary infections. The results showed that the presence of silver mist was effective in more rapidly clearing the bacterial load of the infected lungs than is the host immune system alone. The apparently less severe pathology associated with the rat lungs treated with the silver mist showed that the treatment was effective for more than simply assisting in the killing of the invading organisms.

Example 5

Pulmonary Anti-Inflammatory Activity

A solution from nanocrystalline silver coated dressings (AgHDPE) from Example 1 was prepared by sparging $CO_2$ through 1000 ml of reverse osmosis water using commercial $CO_2$ Soda Syphon Charger. This process resulted in the pH of the water dropping to about 4. At this point, approximately 333 ml of the carbonated water was decanted into a plastic bottle and 333 square inches of nanocrystalline silver-coated net was added to the water. The nanocrystalline silver-coated net and water were placed in 37° C. shaker incubator and shaken at 180 RPM for 30 minutes to elevate the pH to approximately 5.8. The solution was then transferred to a beaker and stirred vigorously for 2 minutes to raise the pH to approximately at 7.3. The dissolution solution was transferred to a commercial nebulizer which was connected to a Medical air cylinder with a flow rate of approx. 20 L/min. The outflow of the nebulizer was connected to a animal chamber housing the rats to be dosed. Only the "test" rats (12 randomly assigned animals) received the dosing. The rats received two—½ hour aerosol administrations of the test solution on the day of infection. Thereafter, the test rats were dosed 3 times per day for an additional one and a half days.

Thirty male Sprague-Dawley rats were obtained. These animals are specific-pathogen free and weighed approximately 400 g. The animals are housed in groups of four in plastic cages with wire mesh tops. The rats had access to fresh water and rat chow ad libitum. All animals were maintained in an appropriate facility with 12-hour light/dark cycles and constant temperature and humidity, according to facility standard operating procedures.

The bacteria used for infection of these animals were *Pseudomonas aeruginosa* strain 5588. The dose was previously titrated to ascertain that a dose of up to $10^9$ CFU was not lethal for the animals. The bacteria were grown overnight in Tryptic soy broth, washed once in sterile PBS and resuspend in sterile PBS. The final concentration of the inoculum was $4\times10^9$ CFU/ml.

The rats were anesthetized by inhalation of 2% halothane. A 400 μL volume of bacterial suspension was intratracheally administered into the bronchi of each rat. This was performed non-surgically on intubated animals. The infection process resulted in the instillation of approximately $10^9$ CFU into the lungs of each animal.

The three treatment groups of rats and treatment schedules were as follows:

| | |
|---|---|
| Group 1 | Infected, not treated (12 Rats) |
| Group 2 | Infected, animal will be treated by intramuscularly injection of Tobramycin at 30 mg/kg (12 mg/rat) once daily (12 Rats) |
| Group 3 | Infected and treated, using nanocrystalline silver solution and nebulizer (Nebulized Ag), three times a day (12 Rats) |
| Day One | |
| 10:00 AM | Infection |
| 4:00 PM | First treatment (For Group 2, Nebulized Ag for Group 3) |
| 8:00 PM | Nebulized Ag treatment for Group 3 |
| Day Two | |
| 9.00 AM | Injection treatment for Group 2, Nebulized Ag for Group 3 |
| 1:00 PM | Sacrifice and sample six Rats in each group |
| 3:00 PM | Nebulized Ag treatment for Group 3 |
| 8:00 PM | Nebulized Ag treatment for Group 3 |

-continued

| Day Three | |
|---|---|
| 9.00 AM | Injection treatment for Group 2, Nebulized Ag for Group 3 |
| 1:00 PM | Sacrifice and sample six Rats in each group |

On each day, six rats of each group of animals were sacrificed. The lungs of the animals were aseptically removed, homogenized and plated to determine bacterial levels. Lung samples were collected for histological examination. Three lung homogenates were reserved for silver analysis. Lungs were grossly scored (absent=0, mild=1, moderate=2, and severe=3) based on the degree and involvement of consolidation, hemorrhage, edema and necrosis based upon gross observation.

Histopathology was scored (0–4) based upon the degree of consolidation and inflammation (neutrophil infiltration). The entire right middle lobes of all rats were collected for histopathology. As whole lobes were selected there was no bias toward any sample. All samples were fixed in neutral buffered formalin at the time the lung was removed from the thorax. It was fixed overnight, dehydrated and embedded in wax. Sections were obtained which were hydrated and stained with haematoxylin and eosin.

All sections were examined by a veterinary pathologist who was blinded to the treatment groups, until after the samples were scored and comments were provided. The Scores and comments are provided in Table 5. (0=normal, 1=slight, 2 moderate, 3 severe, 4 very severe).

Tissue Colony Counts:

At 24 hours, there was not a significant reduction in the number of colony forming units (cfu) in the nebulized Ag group compared to the control but at 48 hours there was a significant reduction in the bacterial numbers in the nebulized Ag animals. The Tobramycin treated animals had a similar cfu counts to the controls at time 24 hours and 48 hours.

Gross Pathology:

The severity of the pulmonary damage based on gross tissue observations was more pronounced in the control group than in the Tobramycin and nebulized groups. There was an associated between high lung bacterial counts and lung gross pathology.

TABLE 5

Gross Lung Scores in Animals Receiving Different Treatments

| 24 h animal | Control | Tobramycin | Nebulization |
|---|---|---|---|
| 1 | 0 | 2 | 1 |
| 2 | 0 | 3 | 1 |
| 3 | 3 | 1 | 0 |
| 4 | 3 | 3 | 0 |
| 5 | 2 | 2 | 3 |
| 6 | 3 | 2 | 1 |
| 48 h animal | Control | Tobramycin | Nebulization |
| 7 | 2 | 1 | 1 |
| 8 | 1 | 2 | 1 |
| 9 | 1 | 1 | 0 |
| 10 | 1 | 1 | 0 |
| 11 | 3 | 1 | 1 |
| 12 | Dead | Dead | Dead |

Histopathology of Lung Samples:

Both the control and the Tobramycin treated rats had similar pathology. These are outlined in Table 6. At 24 and 48 hours severe infiltration of polymorphonuclear leukocytes (PMN's) into the interstitial spaces of the lung was observed. These cellular elements could also be identified in alveolar and bronchiolar spaces but to a lesser extent. The pulmonary vessels were dilated and the alveolar spaces were filled with proteinaceous material. The silver-nebulized rats had occasional infiltration of PMN's and no evidence of accumulation of fluids in aveolar or bronchiolar spaces.

TABLE 6

Histopathology of Lung Samples Removed from Rats

| Treatment | Time | Inflam Score | Consol Score | Comments |
|---|---|---|---|---|
| Control (1) | 24 | 3 | 3 | Severe infiltration of PMN' into interstitial spaces. Proteinaceous secretion in alveolar spaces. Occasional PMN in alveolar and bronchiolar space. Consolidation in affected areas. Involvement of 70% of sample. Interstitial Pneumonia. |
| Control (2) | 24 | 3 | 3 | Severe infiltration of PMN's into interstitial spaces. Proteinaceous secretion in alveolar spaces. Occasional PMN in alveolar and bronchiolar space. Consolidation in affected areas. Involvement of 80% of sample. Interstitial Pneumonia. |
| Tobramycin (1) | 24 | 3 | 3 | Severe infiltration of PMN's into interstitial spaces. Proteinaceous secretion in alveolar spaces. Occasional PMN in alveolar and bronchiolar space. Consolidation in affected areas. Involvement of 90% of sample. Interstitial Pneumonia. |
| Tobramycin (2) | 24 | 3 | 3 | Severe infiltration of PMN's into interstitial spaces. Proteinaceous secretion in alveolar spaces. Occasional PMN in alveolar and bronchiolar space. Consolidation in affected areas. Involvement of 80% of sample. Interstitial Pneumonia. |
| Nebulized Ag (1) | 24 | 0 | 1 | No PMN's in area. Slight consolidation. Normal Lung |
| Nebulized Ag (2) | 24 | 1 | 1 | Slight infiltration of PMN's around vessels and brocheoli. |
| Control (1) | 48 | 3 | 3 | Severe infiltration of PMN's into interstitial spaces. Proteinaceous secretion in alveolar spaces. Occasional PMN in alveolar and bronchiolar space. Consolidation in affected areas. Involvement of 80% of sample. Interstitial Pneumonia. |
| Control (2) | 48 | 2 | 2 | Severe infiltration of PMN's into interstitial spaces. Proteinaceous secretion in alveolar spaces. Occasional PMN in alveolar and bronchiolar space. Consolidation in affected areas. Involvement of 60% of sample. Interstitial Pneumonia. |

TABLE 6-continued

Histopathology of Lung Samples Removed from Rats

| Treatment | Time | Inflam Score | Consol Score | Comments |
|---|---|---|---|---|
| Tobramycin (1) | 48 | 3 | 3 | Severe infiltration of PMN's into interstitial spaces. Proteinaceous secretion in alveolar spaces. Occasional PMN in alveolar and bronchiolar space. Consolidation in affected areas. Involvement of 70% of sample. Interstitial Pneumonia. |
| Tobramycin (2) | 48 | 3 | 3 | Severe infiltration of PMN's into interstitial spaces. Proteinaceous secretion in alveolar spaces. Occasional PMN in alveolar and bronchiolar space. Consolidation in affected areas. Involvement of 70% of sample. Interstitial Pneumonia. |
| Nebulized Ag (1) | 48 | 1 | 0 | Slight infiltration of PMN's around vessels and brocheoli. |
| Nebulized Ag (2) | 48 | 0 | 0 | Normal lung |

The nebulized nanocrystalline silver reduced bacterial colonization in Pseudomonas infected lungs reduced injury as determined by gross pathology (consolidation, hemorrhage, edema) in Pseudomonas infected lungs. Further, the nanocrystalline silver delivered by aerosol reduced pulmonary inflammation (primarily PMN infiltration) in Pseudomonas infected lungs compared to Tobramycin (IM).

Example 6

Pulmonary Anti-Inflammatory Activity

A solution was prepared by sparging $CO_2$ through 1000 ml of reverse osmosis water using commercial $CO_2$ Soda Syphon Charger. This process results in the pH of the water dropping to about 4. At this point, approximately 333 ml of the carbonated water was decanted into a plastic bottle and 333 square inches of nanocrystalline silver-coated net was added to the water. The nanocrystalline silver-coated net and water were placed in 37° C. shaker incubator and shaken at 180 RPM for 30 minutes to elevate the pH to approximately 5.8. The solution was then transferred to a beaker and stirred vigorously for 2 minutes to raise the pH to approximately at 7.3. The solution had a final silver concentration of approximately 400 ppm.

Test solutions of silver nitrate (400 ppm) and silver acetate (400 ppm) were prepared by dissolving the silver salts in deionized water. A colloidal silver solution (20 ppm) in was obtained from a commercial source.

The dissolution solutions were transferred to commercial nebulizers which were connected to a Medical air cylinder with a flow rate of approx. 20 L/min. The outflows of the nebulizers were connected to an animal chamber housing the rats to be dosed. All rats (40 randomly assigned animals) received the dosing. The rats received two—½ hour aerosol administrations of the test solutions on the day of infection. Thereafter, the test rats were dosed 3 times per day for an additional one and a half days.

Forty male Sprague-Dawley rats were obtained. These animals are specific-pathogen free and weighed approximately 400 g. The animals were housed in groups of four in plastic cages with wire mesh tops. The rats had access to fresh water and rat chow ad libitum. All animals were maintained in an appropriate facility with 12-hour light/dark cycles and constant temperature and humidity, according to facility standard operating procedures.

The bacteria used for infection of 20 these animals were *Pseudomonas aeruginosa* strain 5588. The dose was previously titrated to ascertain that a dose of up to $10^9$ CFU was not lethal for the animals. The bacteria were grown overnight in Tryptic soy broth, washed once in sterile PBS and resuspend in sterile PBS. The final concentration of the inoculum was $4\times10^9$ CFU/ml.

The rats were anesthetized by inhalation of 2% halothane. A 400 μL volume of bacterial suspension was intratracheally administered into the bronchi of each rat. This was performed non-surgically on intubated animals. The infection process resulted in the instillation of approximately $10^9$ CFU into the lungs of each animal. There were two treatment groups of rats in this study as follows:

Group 1 & 2 Not Infected and infected, treated with nebulized silver nitrate. (10 Rats)

Group 3 & 4 Not infected and infected, treated with nebulized colloidal silver (10 Rats)

Group 5 & 6 Not infected and infected, treated with nebulized nanocrystalline silver. (10 Rats)

Group 7 & 8 Not infected and infected and treated with nebulized silver acetate (10 rats) The treatment schedule was as follows:

| Day One | | Day Two | |
|---|---|---|---|
| 10:00 AM | Infection | 9:00 AM | Third Treatment |
| 4:00 PM | First treatment | 1:00 PM | Sacrifice, sample 5 Rats/Gp |
| 8:00 PM | Second treatment | | |

All rats of each group of animals were sacrificed after 24h. The lungs of the animals were aseptically removed, homogenized and plated to determine bacterial levels. Lung samples were collected for histological examination. Three lung homogenates were reserved for silver analysis. Lungs were grossly scored (absent=0, mild=1, moderate=2, and severe=3) based on the degree and involvement of consolidation, hemorrhage, edema and necrosis based upon gross observation.

Histopathology was scored (0–4) based upon the degree of consolidation and inflammation (neutrophil infiltration). The entire right middle lobes of all rats were collected for histopathology. As whole lobes were selected there was no bias toward any sample. All samples were fixed in neutral buffered formalin at the time the lung was removed from the thorax. It was fixed overnight, dehydrated and embedded in wax. Sections were obtained which were hydrated and stained with haematoxylin and eosin.

All sections were examined by a veterinary pathologist who was blinded to the treatment groups, until after the samples were scored and comments were provided, with scoring being (0=normal, 1=slight, 2 moderate, 3 severe, 4 very severe).

All rats in the silver nitrate, silver acetate and colloidal silver groups had lung that were grossly scored as moderately to severely inflamed while the lungs of the nanocrystalline group were grossly scored as normal to slightly inflamed. This was confirmed by the histopathological analyses.

The nanocrystalline derived silver solution had pulmonary anti-inflammatory properties while the other forms of silver did not.

Example 7

Treatment of an Infected Throat with a Nanocrystalline Silver Derived Solution A forty-nine year old male was suffering from an infected throat. The condition was accompanied by fever and a severe pain that made swallowing very difficult and limited the patients ability to sleep. A solution of nanocrystalline derived silver was prepared using a method similar to Example 1. This solution was gargled for one minute and repeated 3 times over the next ten minutes. Within an hour the pain was reduced to the point where the patient could sleep. The treatment was repeated every four hours for 16 h and then once 8 h later. The throat infection was cleared as determined by the elimination of fever and pain. No further symptoms occurred.

Example 8

Preparation of Gels

No. 1—A commercial carboxymethyl cellulose/pectin gel (DuoDERM™, ConvaTec Canada, 555, Dr. Frederik Philips, Suite 110, St-Laurent, Quebec, H4M 2×4) was combined with nanocrystalline silver powder prepared as set forth in Example 2 to produce a gel with 0.1% silver. A logarithmic reduction test was performed as follows in the gel using *Pseudomonas aeruginosa*. The inoculum was prepared by placing 1 bacteriologic loopful of the organism in 5 ml of trypticase soy broth and incubating it for 3–4 h. The inoculum (0.1 ml) was then added to 0.1 ml of gel and vortexed (triplicate samples). The mixture was incubated for one-half hour. Then 1.8 ml of sodium thioglycollate-saline (STS) solution was added to the test tube and vortexed. Serial dilutions were prepared on $10^{-1}$ to $10^{-7}$. A 0.1 ml aliquot of each dilution was plated in duplicate into Petri plates containing Mueller-Hinton agar. The plates were incubated for 48 h and then colonies were counted. Surviving members of organisms were determined and the logarithmic reduction compared to the initial inoculum was calculated. The logarithmic reduction for this mixture was 6.2, indicating a significant bactericidal effect.

No. 2—Carboxymethyl cellulose (CMC) fibers were coated directly to produce an atomic disordered nanocrystalline silver coating, using magnetron sputtering conditions similar to those set forth in Example 1. The CMC was then gelled in water by adding 2.9 g to 100 ml volume. This material was tested using the method of No. 1. The material generated a 5.2 logarithmic reduction of *Pseudomonas aeruginosa,* demonstrating that the gel had a significant bactericidal effect.

No. 3—An alginate fibrous substrate was directly coated with an atomic disordered nanocrystalline silver coating using magnetron sputtering conditions similar to those set forth in Example 1. The alginate (5.7 g) was added to 100 ml volume of water to create a gel. This material was tested using the method of No. 1. The material generated a 5.2 logarithmic reduction of *Pseudomonas aeruginosa,* demonstrating that the gel had a significant bactericidal effect.

No. 4—A commercial gel containing CMC and alginate (Purilin gel, Coloplast) was mixed with a atomic disordered nanocrystalline silver powder to give a product with 0.1% silver. This was tested as above with both *Pseudomonas aeruginosa* and *Staphylococcus aureus.* Zone of inhibition data was also generated for this gel as follows. An inoculum (*Pseudomonas aeruginosa* and *Staphylococcus aureus*) was prepared as in No. 1 and 0.1 ml of this was spread onto the surface of Mueller-Hinton agar in a Petri dish. A six mm hole was then cut into the agar at the center of the Petri dish and removed. The well was filled with either 0.1 ml of the silver containing gel, a mupirocin containing cream or a mupirocin containing ointment. The Petri plates were then incubated for 24 h and the diameter of the zone of inhibition was measured and recorded. The silver containing gel produced 9 mm zone of inhibition against both *Pseudomonas aeruginosa* and *Staphylococcus aureus,* while the mupirocin cream and ointment produced 42 and 48 mm zones against *Staphylococcus aureus* and 0 mm zones against *Pseudomonas aeruginosa.* The silver containing gel reduced the *Pseudomonas aeruginosa* and *Staphylococcus aureus* properties by 4.4 and 0.6 log reductions, respectively, showing good bactericidal activity. The mupirocin cream and ointment generated 0.4 and 0.8, and 0.8 and 1.6, log reductions against *Staphylococcus aureus* and *Pseudomonas aeruginosa,* respectively. The silver gel had both a greater bactericidal effect and spectrum of activity than the mupirocin containing products.

Nos. 5–10—The formula for Nos. 5–10 are summarized in Table 7. Zones of inhibitions were determined as in No. 4 and log reductions as in No. 1. All formulae provided a broader spectrum of activity and a greater bactericidal effect than did mupirocin in a cream or ointment form. The mupirocin cream produced zones of inhibition of 42 and 0, and log reduction of 0.4 and 0.8, against *Staphylococcus aureus* and *Pseudomonas aeruginosa,* respectively.

TABLE 7

Formulae for Gel Nos. 5–10 and Efficacy Results

| # | CMC (%) | PVA (%) | Silver (%) | β-glucan | Methyl paraben | Propyl paraben | CZOI *S. aureus* | CZOI *P. aeruginosa* | Log Red'n *S. aureus* | Log Red'n *P. aeruginosa* |
|---|---|---|---|---|---|---|---|---|---|---|
| 5 | 2 | | 0.1 | | | | 11 | 13 | 1.4 | >6 |
| 6 | 2 | 0.5 | 0.1 | | 0.1 | 0.02 | 14 | 15 | 3.3 | >6 |

TABLE 7-continued

Formulae for Gel Nos. 5–10 and Efficacy Results

| # | CMC (%) | PVA (%) | Silver (%) | β-glucan | Methyl paraben | Propyl paraben | CZOI S. aureus | CZOI P. aeruginosa | Log Red'n S. aureus | Log Red'n P. aeruginosa |
|---|---|---|---|---|---|---|---|---|---|---|
| 7 | 2 | 0.5 | 0.1 | | | | 13 | 14 | 2 | N/A |
| 8 | 2 | 0.5 | 0.1 | | 0.1 | | 14 | 14 | 2 | N/A |
| 9 | 2 | 0.5 | 0.1 | | | 0.20 | 14 | 14 | 2 | N/A |
| 10 | 2 | 0.5 | 0.1 | 0.5 | 0.1 | 0.20 | 14 | 14 | 2 | >6 |

No. 11—A commercially available gel (glyceryl polymethacrylate) was blended with nanocrystalline silver powder from Example 2 to produce a gel with a silver content of 0.1%. This gel was tested as in Nos. 5–10 and was found to produce zones of 15 mm against both *Staphylococcus aureus* and *Pseudomonas aeruginosa*. Log reductions of 1.7 and>5 were produced against *Staphylococcus aureus* and *Pseudomonas aeruginosa*. This gel product had a greater spectrum of activity than did mupirocin cream or ointment.

The silver gel solutions of No. 1–11 can be used as gel formulations for the treatment of mucosal membranes in accordance with the present invention.

All publications mentioned in this specification are indicative of the level of skill of those skilled in the art to which this invention pertains and. All publications are herein incorporated by reference to the same extent as if each individual publication was specifically and individually indicated to be incorporated by reference.

The terms and expressions in this specification are, unless otherwise specifically defined herein, used as terms of description and not of limitation. There is no intention, in using such terms and expressions, of excluding equivalents of the features illustrated and described, it being recognized that the scope of the invention is defined and limited only by the claims which follow.

We claim:

1. A method of reducing inflammation or infection of a mucosal membrane, comprising:

contacting an inflamed or infected problem area of the mucosal membrane with a therapeutically effective amount of one or more antimicrobial metals in nanocrystalline form to provide a localized anti-inflammatory or antimicrobial effect, wherein the one or more antimicrobial metals are selected from the group consisting of silver, gold, platinum and palladium and characterized by sufficient atomic disorder so that the metal, in contact with an alcohol or water-based electrolyte, releases atoms, ions, molecules, or clusters of said metal on a sustainable basis and at a concentration sufficient to provide a localized anti-inflammatory or antimicrobial effect.

2. The method of claim 1, wherein the one or more antimicrobial metals provide a localized antimicrobial effect.

3. The method of claim 2, wherein the mucosal membrane is one or more of the oral cavity, the nasal, bronchial, pulmonary, trachea and pharynx airways, the otic and ophthalmic surfaces, the urogenital system, the reproductive system, and the gastrointestinal tract.

4. The method of claim 2, wherein the mucosal membrane is the oral cavity, the nasal, bronchial, pulmonary, trachea and pharynx airways, the urogenital system, the reproductive system, or the gastrointestinal tract.

5. The method of claim 2, wherein the mucosal membrane is the prostate, the colon or rectal surfaces.

6. The method of claim 1, wherein the antimicrobial metal is nanocrystalline silver.

7. The method of claim 1, wherein the antimicrobial metal is nanocrystalline silver, formed as a composite with oxygen.

8. The method of claim 1, wherein the antimicrobial metal is delivered as a powder, aerosol, spray, mist to the oral cavity, or to an area of the nasal, bronchial, pulmonary, trachea or pharynx airways to a respiratory disorder.

9. The method of claim 8, wherein the antimicrobial metal is nanocrystalline silver delivered as an aerosol, wherein the aerosol has a droplet size which is less than 10 μm, and wherein the concentration of silver in the aerosol is in the range of 40 to 500 μg/ml.

10. The method of claim 9, wherein the aerosol does not contain particulates sized larger than 2 μm.

11. The method of claim 10, wherein the aerosol does not contain particulates sized larger than 1 μm.

12. The method of claim 1, wherein the one or more antimicrobial metals are provided as a coating on, or filler in, a dressing, substrate or patch, or in a pharmaceutical composition with one or more pharmaceutically acceptable carriers suitable for application to the mucosal membrane.

13. The method of claim 12, wherein the pharmaceutical composition includes a nanocrystalline powder of the one or more antimicrobial metals, or a liquid containing dissolved species from a nanocrystalline powder or coating of the one or more antimicrobial metals.

14. The method of claim 13, wherein the pharmaceutical composition is a one or more of a gel, cream, lotion, paste, ointment, foam, suppository, lozenge, gum, tablet, capsule, or wafer containing the antimicrobial metal powder in an amount of 0.01–10% by weight, or one or more of a liquid formulated as a topical solution, aerosol, instillation, infusion, spray, mist, drops, syrup, elixir, mouth wash, or retention enema containing 0.001–10% by weight of the antimicrobial metal.

15. The method of claim 14, wherein the mucosal membrane is contacted to treat a respiratory disorder, a disease or condition of the oral cavity, a gastrointesinal disorder, a nasal disorder, or a disorder of the urogenital or reproductive system.

16. The method of claim 15, wherein the antimicrobial metal is nanocrystalline silver.

17. The method of claim 15, wherein the antimicrobial metal is silver, formed as a composite with oxygen.

18. The method of claim 12, wherein the dressing or pharmaceutical composition is fixed in place or occluded with an occlusive or semi-occlusive layer which maintains the dressing or composition in a moist condition.

19. The method of claim 12, wherein the one or more antimicrobial metals are provided in a hydrated or hydrocolloid-containing dressing, or in a pharmaceutical composition with one or more hydrocolloids.

20. The method of claim 19, wherein the hydrocolloid is one or more of cellulose and derivatives thereof, starch, glycogen, gelatin, pectin, alginate, chitosan, chitin, gum arabic, locust bean gum, karaya gum, gum tragacanth, ghatti gum, agar-agar, carrageenans, carob gum, guar gum, and xanthan gum.

21. The method of claim 20, wherein the hydrocolloid is one or more of carboxymethyl cellulose, alginate, pectin, and glyceryl polymethacrylate.

22. The method of claim 21, wherein the antimicrobial metal is nanocrystalline silver.

23. The method of claim 21, wherein the antimicrobial metal is nanocrystalline silver, formed as a composite with oxygen.

24. The method of claim 1, wherein the antimicrobial metal is in a powder form and is delivered directly to the mucosal membrane.

25. The method of claim 24, wherein the powder is sized with particulates no larger than 2 μm.

26. The method of claim 25, wherein the powder is sized with particulates no larger than 1 μm.

27. The method of claim 26, wherein the antimicrobial metal is nanocrystalline silver.

28. The method of claim 26, wherein the antimicrobial metal is nanocrystalline silver, formed as a composite with oxygen.

* * * * *